United States Patent
Gasser et al.

(10) Patent No.: US 11,359,223 B2
(45) Date of Patent: Jun. 14, 2022

(54) EXPRESSION SEQUENCES

(71) Applicant: Lonza LTD, Visp (CH)

(72) Inventors: Brigitte Gasser, Vienna (AT); Diethard Mattanovich, Vienna (AT); Silvia Heiss, Vienna (AT)

(73) Assignee: LONZA LTD, Visp (CH)

( * ) Notice: Subject to any disclaimer, the term of this patent is extended or adjusted under 35 U.S.C. 154(b) by 0 days.

(21) Appl. No.: 15/860,186

(22) Filed: Jan. 2, 2018

(65) Prior Publication Data
US 2018/0135092 A1 May 17, 2018

Related U.S. Application Data

(63) Continuation of application No. 14/435,581, filed as application No. PCT/EP2013/072572 on Oct. 29, 2013, now Pat. No. 10,160,988.

(30) Foreign Application Priority Data

Oct. 29, 2012 (EP) .................................... 12190361

(51) Int. Cl.
| C12P 21/02 | (2006.01) |
| C12P 21/06 | (2006.01) |
| C12P 21/08 | (2006.01) |
| C07K 16/00 | (2006.01) |
| C12N 15/81 | (2006.01) |
| C07K 14/39 | (2006.01) |
| C07K 14/435 | (2006.01) |
| C07K 14/765 | (2006.01) |
| C12N 9/64 | (2006.01) |

(52) U.S. Cl.
CPC .............. *C12P 21/02* (2013.01); *C07K 14/39* (2013.01); *C07K 14/43595* (2013.01); *C07K 14/765* (2013.01); *C07K 16/00* (2013.01); *C12N 9/6478* (2013.01); *C12N 15/815* (2013.01); *C07K 2317/56* (2013.01)

(58) Field of Classification Search
None
See application file for complete search history.

(56) References Cited

U.S. PATENT DOCUMENTS

| 5,268,273 A | 12/1993 | Buckholz |
| 7,741,075 B2 | 6/2010 | Inan |
| 10,160,988 B2 * | 12/2018 | Gasser ................... C07K 14/39 |
| 2011/0021378 A1 | 1/2011 | Callewaert et al. |

FOREIGN PATENT DOCUMENTS

| EP | 0438200 A1 | 7/1991 |
| EP | 0301669 B1 | 6/1993 |
| EP | 0324274 B1 | 11/1993 |
| EP | 0792367 B1 | 10/2001 |
| EP | 2258855 A1 | 8/2010 |
| WO | 8401153 A1 | 3/1984 |
| WO | 2008128701 A2 | 10/2008 |
| WO | 2010135678 A1 | 11/2010 |
| WO | 2011073367 A1 | 6/2011 |
| WO | 2012152823 A1 | 11/2012 |

OTHER PUBLICATIONS

Rahbarizadeh et al., "Over expression of anti-MUC1 single-domain antibody fragments", Mol. Immunol. 43:426-435, 2006 (Year: 2006).*
Ghosalkar et al., "Secretory expression of interferon-alpha 2b in recombinant *Pichia pastoris* using three different secretion signals", Prot. Exp. Purif. 60:103-109, 2008 (Year: 2008).*
Lange et al., J. Immun. Methods 255:103-114, 2001 (Year: 2001).*
Bader, et al., "Processing of predicted substrates of fungal Kex2 proteinases from *Candida albicans, C. glabrata, Saccharomyces cerevisiae* and *Pichia pastoris*", BMC Microbiology, 2008 vol. 8: p. 116.
De Schutter, et al., "Genome sequence of the recombinant protein production host *Pichia pastoris*", Nature Biotechnology, vol. 27, No. 6, Jun. 2009, p. 561.
Heiss, et al., "Identification and deletion of the major secreted protein of *Pichia pastoris*", Appl Microbiol Biotechnol, vol. 97, p. 1241, 2013.
Khasa, et al., "Isolation of *Pichia pastoris* PIR genes and their utilization for cell surface display and recombinant protein secretion", Yeast, vol. 28, p. 213, 2011.
Kobayashi, "Summary of recombinant human serum albumin development", Biologicals, vol. 34, p. 55, 2006.
Kottmeier, et al., "Hydrophobin signal sequence mediates efficient secretion of recombinant proteins in *Pichia pastoris*", Applied Microbiol Biotechnol, vol. 91, p. 133, 2011.
Stadlmayr, et al., "Identification and characterisation of novel *Pichia pastoris* promoters for heterologous protein production", Journal of Biotechnology, vol. 150, p. 519, 2010.
Partial European Search Report issued in European Application No. EP12190361 dated Mar. 5, 2013.
Extended European Search Report issued in European Application No. EP 12190361 dated Jun. 20, 2013.
International Search Report and Written Opinion, issued in Application No. PCT/EP2013/072572 dated Jan. 14, 2014.
International Preliminary Report on Patentability, issued in Application No. PCT/EP2013/072572 dated May 5, 2015.

(Continued)

*Primary Examiner* — David Steadman
(74) *Attorney, Agent, or Firm* — Medler Ferro Woodhouse & Mills

(57) ABSTRACT

An isolated nucleic acid encoding a leader, which has a specific sequence, an isolated leader peptide encoded by such nucleic acid, an expression cassette comprising such nucleic acid encoding a leader operably linked to a nucleic acid sequence encoding a POI a recombinant yeast host cell or a vector comprising such expression cassette, a method of producing a POI in such yeast host cell, and further the use of the specific nucleic acid for the secretion of a POT from a host cell and/or to increase the secretion of a POT from a host cell.

9 Claims, 5 Drawing Sheets

Figure 2A:
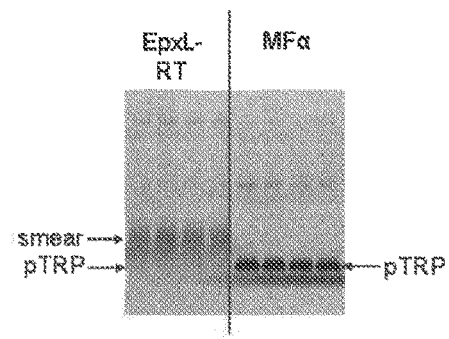

Specification includes a Sequence Listing.

(56) References Cited

OTHER PUBLICATIONS

Heiss, "Establishment and characterization of a novel secretion system in the methylotrophic yeast *Pichia pastoris*", 2011, Diplomarbeit University Vienna; URL: http://othes.univie.ac.at/13923/1/2011-03-27_0404984.pdf, 101 pages.
Heiss et al., "Multistep processing of the secretion leader of the extracellular protein Epx1 in *Pichia pastoris* and Implications for protein localization", Microbiology. Jul. 2015;161(7):1356-68.
De Schutter K et al. Nature Biotechnology Jun. 2009;27(6):561-6. doi: 10.1038/nbt.1544. Epub May 24, 2009, supplemental.
U.S. Patent and Trademark Office. Non-Final Office Action issued in U.S. Appl. No. 14/435,581 dated Mar. 14, 2018. 25 pages.

* cited by examiner

Fig. 1: pG1 promotor (SEQ ID 9)

ATTTCCACCCCCATCCCAGTAGAATGTAGGGTCCCCAAACATTTGCTCCCCTAG
TCTCCAGGGAAATGTAAAATATACTGCTAATAGAAAACAGTAAGACGCTCAGTTGT
CAGGATAATTACGTTCGACTGTAGTAAAACAGGAATCTGTATTGTTAGAAAGAACG
AGAGTTTTTTACGGCGCCGCCATATTGGGCCGTGTGAAAACAGCTTGAAACCCCA
CTACTTTCAAAGGTTCTGTTGCTATACACGAACCATGTTTAACCAACCTCGCTTTT
GACTTGACTGAAGTCATCGGTTAACAATCAAGTACCCTAGTCTGTCTGAATGCTCC
TTTCCATATTCAGTAGGTGTTTCTTGCACTTTTGCATGCACTGCGGAAGAATTAGC
CAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCT
GAAAAAACTGCAGATAGACTTCAAGATCTCAGGGATTCCCACTATTTGGTATTCTG
ATATGTTTTCCTGATATGCATCAAAACTCTAATCTAAACCTGAATCTCCGCTATT
TTTTTTTTTTTTGATGACCCCGTTTTCGTGACAAATTAATTTCCAACGGGGTCTT
GTCCGGATAAGAGAATTTTGTTTGATTATCCGTTCGGATAAATGGACGCCTGCTCC
ATATTTTTCCGGTTATTACCCCACCTGGAAGTGCCCAGAATTTTCCGGGGATTACG
GATAATACGGTGGTCTGGATTAATTAATACGCCAAGTCTTACATTTTGTTGCAGTC
TCGTGCGAGTATGTGCAATAATAAACAAGATGAGCCAATTTATTGGATTAGTTGCA
GCTTGACCCCGCCATAGCTAGGCATAGCCAAGTGCTATGGGTGTTAGATGATGCA
CTTGGATGCAGTGAGTTTTGGAGTATAAAGATCCTTAAAATTCCACCCTT

SEQUENCE LISTING

```
<160> NUMBER OF SEQ ID NOS: 53

<210> SEQ ID NO 1
<211> LENGTH: 20
<212> TYPE: PRT
<213> ORGANISM: Pichia pastoris
<220> FEATURE:
<221> NAME/KEY: PEPTIDE
<222> LOCATION: (3)..(3)
<223> OTHER INFORMATION: X is either F or L
<220> FEATURE:
<221> NAME/KEY: PEPTIDE
<222> LOCATION: (16)..(16)
<223> OTHER INFORMATION: X is either A or T

<400> SEQUENCE: 1

Met Lys Xaa Ser Thr Asn Leu Ile Leu Ala Ile Ala Ala Ala Ser Xaa
1               5                   10                  15

Val Val Ser Ala
            20
```

<210> SEQ ID NO 2
<211> LENGTH: 20
<212> TYPE: PRT
<213> ORGANISM: Pichia pastoris

<400> SEQUENCE: 2

Met Lys Leu Ser Thr Asn Leu Ile Leu Ala Ile Ala Ala Ala Ser Ala
1               5                   10                  15

Val Val Ser Ala
            20

<210> SEQ ID NO 3
<211> LENGTH: 20
<212> TYPE: PRT
<213> ORGANISM: Pichia pastoris

<400> SEQUENCE: 3

Met Lys Phe Ser Thr Asn Leu Ile Leu Ala Ile Ala Ala Ala Ser Ala
1               5                   10                  15

Val Val Ser Ala
            20

<210> SEQ ID NO 4
<211> LENGTH: 20
<212> TYPE: PRT
<213> ORGANISM: Pichia pastoris

<400> SEQUENCE: 4

Met Lys Phe Ser Thr Asn Leu Ile Leu Ala Ile Ala Ala Ala Ser Thr
1               5                   10                  15

Val Val Ser Ala
            20

<210> SEQ ID NO 5
<211> LENGTH: 20
<212> TYPE: PRT
<213> ORGANISM: Pichia pastoris

<400> SEQUENCE: 5

Met Lys Leu Ser Thr Asn Leu Ile Leu Ala Ile Ala Ala Ala Ser Thr
1               5                   10                  15

Val Val Ser Ala
            20

<210> SEQ ID NO 6
<211> LENGTH: 5
<212> TYPE: PRT
<213> ORGANISM: Pichia pastoris

<400> SEQUENCE: 6

Val Ser Ala Ala Pro
1               5

<210> SEQ ID NO 7
<211> LENGTH: 16
<212> TYPE: PRT
<213> ORGANISM: Pichia pastoris

<400> SEQUENCE: 7

Ala Pro Val Ala Pro Ala Glu Glu Ala Ala Asn His Leu His Lys Arg
1               5                   10                  15

<210> SEQ ID NO 8
<211> LENGTH: 57
<212> TYPE: PRT
<213> ORGANISM: Pichia pastoris

<400> SEQUENCE: 8

Met Lys Phe Ser Thr Asn Leu Ile Leu Ala Ile Ala Ala Ala Ser Thr
1               5                   10                  15

Val Val Ser Ala Ala Pro Val Ala Pro Ala Glu Glu Ala Ala Asn His
            20                  25                  30

Leu His Lys Arg Ala Tyr Tyr Thr Asp Thr Thr Lys Thr His Thr Phe
        35                  40                  45

Thr Glu Val Val Thr Val Tyr Arg Thr
    50                  55

<210> SEQ ID NO 9
<211> LENGTH: 1001
<212> TYPE: DNA
<213> ORGANISM: Pichia pastoris

<400> SEQUENCE: 9
atttccaccc ccatcccagt agaatgtagg gtccccaaac atttgctccc cctagtctcc      60
agggaaatgt aaaatatact gctaatagaa aacagtaaga cgctcagttg tcaggataat     120
tacgttcgac tgtagtaaaa caggaatctg tattgttaga agaacgaga gttttttacg     180 gcgccgccat attgggccgt gtgaaaacag cttgaaaccc cactactttc aaaggttctg     240
ttgctataca cgaaccatgt ttaaccaacc tcgcttttga cttgactgaa gtcatcggtt     300
aacaatcaag taccctagtc tgtctgaatg ctcctttcca tattcagtag gtgtttcttg     360
cacttttgca tgcactgcgg aagaattagc caatagcgcg tttcatatgc gcttttaccc     420
cctcttttgt caagcgcaaa atgcctgtaa gatttggtgg gggtgtgagc cgttagctga     480
agtacaacag gctaattccc tgaaaaaact gcagatagac ttcaagatct cagggattcc     540
cactatttgg tattctgata tgttttttcct gatatgcatc aaaactctaa tctaaaacct     600
gaatctccgc tattttttttt ttttttttga tgaccccgtt ttcgtgacaa attaatttcc     660 aacgggtct tgtccggata agagaatttt gtttgattat ccgttcggat aaatggacgc     720
ctgctccata ttttccggt tattacccca cctggaagtg cccagaattt tccggggatt     780
acggataata cggtggtctg gattaattaa tacgccaagt cttacatttt gttgcagtct     840
cgtgcgagta tgtgcaataa taaacaagat gagccaattt attggattag ttgcagcttg     900
accccgccat agctaggcat agccaagtgc tatgggtgtt agatgatgca cttggatgca     960
gtgagttttg gagtataaaa gatccttaaa attccaccct t                        1001

<210> SEQ ID NO 10
<211> LENGTH: 36
<212> TYPE: PRT
<213> ORGANISM: Pichia pastoris
<220> FEATURE:
<221> NAME/KEY: PEPTIDE
<222> LOCATION: (3)..(3)
<223> OTHER INFORMATION: X is either F or L
<220> FEATURE:
<221> NAME/KEY: PEPTIDE
<222> LOCATION: (16)..(16)
<223> OTHER INFORMATION: X is either A or T

<400> SEQUENCE: 10

Met Lys Xaa Ser Thr Asn Leu Ile Leu Ala Ile Ala Ala Ala Ser Xaa

```
                1               5                  10                 15
Val Val Ser Ala Ala Pro Val Ala Pro Ala Glu Glu Ala Ala Asn His
            20                  25                 30

Leu His Lys Arg
        35

<210> SEQ ID NO 11
<211> LENGTH: 36
<212> TYPE: PRT
<213> ORGANISM: Pichia pastoris

<400> SEQUENCE: 11

Met Lys Leu Ser Thr Asn Leu Ile Leu Ala Ile Ala Ala Ala Ser Ala
1               5                  10                 15

Val Val Ser Ala Ala Pro Val Ala Pro Ala Glu Glu Ala Ala Asn His
            20                  25                 30

Leu His Lys Arg
        35

<210> SEQ ID NO 12
<211> LENGTH: 36
<212> TYPE: PRT
<213> ORGANISM: Pichia pastoris

<400> SEQUENCE: 12

Met Lys Phe Ser Thr Asn Leu Ile Leu Ala Ile Ala Ala Ala Ser Ala
1               5                  10                 15

Val Val Ser Ala Ala Pro Val Ala Pro Ala Glu Glu Ala Ala Asn His
            20                  25                 30

Leu His Lys Arg
        35

<210> SEQ ID NO 13
<211> LENGTH: 36
<212> TYPE: PRT
<213> ORGANISM: Pichia pastoris

<400> SEQUENCE: 13

Met Lys Phe Ser Thr Asn Leu Ile Leu Ala Ile Ala Ala Ala Ser Thr
1               5                  10                 15

Val Val Ser Ala Ala Pro Val Ala Pro Ala Glu Glu Ala Ala Asn His
            20                  25                 30

Leu His Lys Arg
        35

<210> SEQ ID NO 14
<211> LENGTH: 36
<212> TYPE: PRT
<213> ORGANISM: Pichia pastoris

<400> SEQUENCE: 14

Met Lys Leu Ser Thr Asn Leu Ile Leu Ala Ile Ala Ala Ala Ser Thr
1               5                  10                 15

Val Val Ser Ala Ala Pro Val Ala Pro Ala Glu Glu Ala Ala Asn His
            20                  25                 30

Leu His Lys Arg
        35

<210> SEQ ID NO 15
<211> LENGTH: 60
```

-continued

```
<212> TYPE: DNA
<213> ORGANISM: Pichia pastoris

<400> SEQUENCE: 15
atgaagctct ccaccaattt gattctagct attgcagcag cttccgccgt tgtctcagct    60

<210> SEQ ID NO 16
<211> LENGTH: 60
<212> TYPE: DNA
<213> ORGANISM: Pichia pastoris

<400> SEQUENCE: 16
atgaagttct ctaccaattt gattctagct attgcagcag cttccgccgt tgtctcagct    60

<210> SEQ ID NO 17
<211> LENGTH: 60
<212> TYPE: DNA
<213> ORGANISM: Pichia pastoris

<400> SEQUENCE: 17
atgaagttct ctaccaattt gatcttagct attgcagcag catccactgt tgtctcagct    60

<210> SEQ ID NO 18
<211> LENGTH: 108
<212> TYPE: DNA
<213> ORGANISM: Pichia pastoris

<400> SEQUENCE: 18
atgaagctct ccaccaattt gattctagct attgcagcag cttccgccgt tgtctcagct    60
gctccagttg ctccagccga agaggcagca aaccacttgc acaagcgt              108

<210> SEQ ID NO 19
<211> LENGTH: 108
<212> TYPE: DNA
<213> ORGANISM: Pichia pastoris

<400> SEQUENCE: 19
atgaagttct ctaccaattt gattctagct attgcagcag cttccgccgt tgtctcagct    60
gctccagttg ctccagccga agaggcagca aaccacttgc acaagcgt              108

<210> SEQ ID NO 20
<211> LENGTH: 108
<212> TYPE: DNA
<213> ORGANISM: Pichia pastoris

<400> SEQUENCE: 20
atgaagttct ctaccaattt gatcttagct attgcagcag catccactgt tgtctcagct    60
gctccagttg ctccagccga agaggcagca aaccacttgc acaagcgt              108

<210> SEQ ID NO 21
<211> LENGTH: 21
<212> TYPE: PRT
<213> ORGANISM: Pichia pastoris

<400> SEQUENCE: 21

Met Lys Leu Ser Thr Asn Leu Ile Leu Ala Ile Ala Ala Ala Ser Ala
1               5                   10                  15

Val Val Ser Ala Ala
            20

<210> SEQ ID NO 22
```

```
<211> LENGTH: 36
<212> TYPE: DNA
<213> ORGANISM: artificial
<220> FEATURE:
<223> OTHER INFORMATION: primer

<400> SEQUENCE: 22
tatacctgca ggatgaagtt ctctaccaat ttgatc                              36

<210> SEQ ID NO 23
<211> LENGTH: 31
<212> TYPE: DNA
<213> ORGANISM: artificial
<220> FEATURE:
<223> OTHER INFORMATION: primer

<400> SEQUENCE: 23
gaagatgcat cgtacggtag acagtgacaa c                                   31

<210> SEQ ID NO 24
<211> LENGTH: 28
<212> TYPE: DNA
<213> ORGANISM: artificial
<220> FEATURE:
<223> OTHER INFORMATION: primer

<400> SEQUENCE: 24
ataccgtacg actgacgacg acgacaag                                       28

<210> SEQ ID NO 25
<211> LENGTH: 40
<212> TYPE: DNA
<213> ORGANISM: artificial
<220> FEATURE:
<223> OTHER INFORMATION: primer

<400> SEQUENCE: 25
ttttggccga ggcggccttt cagttagcag cgatagtttg                          40

<210> SEQ ID NO 26
<211> LENGTH: 37
<212> TYPE: DNA
<213> ORGANISM: artificial
<220> FEATURE:
<223> OTHER INFORMATION: primer

<400> SEQUENCE: 26
aggcgtctac cgaactgatg cacacaagag tgaggtt                             37

<210> SEQ ID NO 27
<211> LENGTH: 39
<212> TYPE: DNA
<213> ORGANISM: artificial
<220> FEATURE:
<223> OTHER INFORMATION: primer

<400> SEQUENCE: 27
gagtggccga ggcggcctta taagcctaag gcagcttga                           39

<210> SEQ ID NO 28
<211> LENGTH: 35
<212> TYPE: DNA
<213> ORGANISM: artificial
<220> FEATURE:
<223> OTHER INFORMATION: primer

<400> SEQUENCE: 28
```

```
atttgtctac cgaactgtga gcaagggcga ggagc                              35
```

<210> SEQ ID NO 29
<211> LENGTH: 39
<212> TYPE: DNA
<213> ORGANISM: artificial
<220> FEATURE:
<223> OTHER INFORMATION: primer

<400> SEQUENCE: 29

```
cgttggccga ggcggcctta cttgtacagc tcgtccatg                          39
```

<210> SEQ ID NO 30
<211> LENGTH: 7
<212> TYPE: PRT
<213> ORGANISM: artificial
<220> FEATURE:
<223> OTHER INFORMATION: peptide

<400> SEQUENCE: 30

Asp Ala His Lys Ser Glu Val
1               5

<210> SEQ ID NO 31
<211> LENGTH: 4
<212> TYPE: PRT
<213> ORGANISM: artificial
<220> FEATURE:
<223> OTHER INFORMATION: peptide

<400> SEQUENCE: 31

Ala Tyr Tyr Thr
1

<210> SEQ ID NO 32
<211> LENGTH: 58
<212> TYPE: DNA
<213> ORGANISM: artificial
<220> FEATURE:
<223> OTHER INFORMATION: primer

<400> SEQUENCE: 32

```
attcgccgaa gaggcagcaa accacttgca caagcgtgat gcacacaaga gtgaggtt    58
```

<210> SEQ ID NO 33
<211> LENGTH: 39
<212> TYPE: DNA
<213> ORGANISM: artificial
<220> FEATURE:
<223> OTHER INFORMATION: primer

<400> SEQUENCE: 33

```
gagtggccga ggcggcctta taagcctaag gcagcttga                          39
```

<210> SEQ ID NO 34
<211> LENGTH: 75
<212> TYPE: DNA
<213> ORGANISM: artificial
<220> FEATURE:
<223> OTHER INFORMATION: primer

<400> SEQUENCE: 34

```
ataccagctg ctccagttgc tccagccgaa gaggcagcaa accacttgca caagcgtact   60
gacgacgacg acaag                                                    75
```

<210> SEQ ID NO 35
<211> LENGTH: 40
<212> TYPE: DNA
<213> ORGANISM: artificial
<220> FEATURE:
<223> OTHER INFORMATION: primer

<400> SEQUENCE: 35
ttttggccga ggcggccttt cagttagcag cgatagtttg  40

<210> SEQ ID NO 36
<211> LENGTH: 76
<212> TYPE: DNA
<213> ORGANISM: artificial
<220> FEATURE:
<223> OTHER INFORMATION: primer

<400> SEQUENCE: 36
ataccagctg ctccagttgc tccagccgaa gaggcagcaa accacttgca caagcgtgtg  60
agcaagggcg aggagc  76

<210> SEQ ID NO 37
<211> LENGTH: 39
<212> TYPE: DNA
<213> ORGANISM: artificial
<220> FEATURE:
<223> OTHER INFORMATION: primer

<400> SEQUENCE: 37
cgttggccga ggcggcctta cttgtacagc tcgtccatg  39

<210> SEQ ID NO 38
<211> LENGTH: 49
<212> TYPE: DNA
<213> ORGANISM: artificial
<220> FEATURE:
<223> OTHER INFORMATION: primer

<400> SEQUENCE: 38
ataagccgaa gaggcagcaa accacttgca caagcgtgac atcgttttg  49

<210> SEQ ID NO 39
<211> LENGTH: 39
<212> TYPE: DNA
<213> ORGANISM: artificial
<220> FEATURE:
<223> OTHER INFORMATION: primer

<400> SEQUENCE: 39
ctatggccga ggcggcccta ttaacactca cctctgttg  39

<210> SEQ ID NO 40
<211> LENGTH: 49
<212> TYPE: DNA
<213> ORGANISM: artificial
<220> FEATURE:
<223> OTHER INFORMATION: primer

<400> SEQUENCE: 40
ataagccgaa gaggcagcaa accacttgca caagcgtgac gttcaattg  49

<210> SEQ ID NO 41
<211> LENGTH: 39
<212> TYPE: DNA
<213> ORGANISM: artificial

```
<220> FEATURE:
<223> OTHER INFORMATION: primer

<400> SEQUENCE: 41
tatcggccga ggcggcccta ttacttacct ggggacaag                              39

<210> SEQ ID NO 42
<211> LENGTH: 98
<212> TYPE: DNA
<213> ORGANISM: artificial
<220> FEATURE:
<223> OTHER INFORMATION: primer

<400> SEQUENCE: 42
atcacctgca ggatgaagtt ctccaccaat ttgattctag ctattgcagc agcttccgcc       60
gttgtctcag ctgctgacat cgttttgact caatcccc                              98

<210> SEQ ID NO 43
<211> LENGTH: 39
<212> TYPE: DNA
<213> ORGANISM: artificial
<220> FEATURE:
<223> OTHER INFORMATION: primer

<400> SEQUENCE: 43
ctatggccga ggcggcccta ttaacactca cctctgttg                              39

<210> SEQ ID NO 44
<211> LENGTH: 30
<212> TYPE: DNA
<213> ORGANISM: artificial
<220> FEATURE:
<223> OTHER INFORMATION: primer

<400> SEQUENCE: 44
ataccagctg ctactgacga cgacgacaag                                        30

<210> SEQ ID NO 45
<211> LENGTH: 40
<212> TYPE: DNA
<213> ORGANISM: artificial
<220> FEATURE:
<223> OTHER INFORMATION: primer

<400> SEQUENCE: 45
ttttggccga ggcggccttt cagttagcag cgatagtttg                             40

<210> SEQ ID NO 46
<211> LENGTH: 31
<212> TYPE: DNA
<213> ORGANISM: artificial
<220> FEATURE:
<223> OTHER INFORMATION: primer

<400> SEQUENCE: 46
gtaccagctg ctgtgagcaa gggcgaggag c                                      31

<210> SEQ ID NO 47
<211> LENGTH: 39
<212> TYPE: DNA
<213> ORGANISM: artificial
<220> FEATURE:
<223> OTHER INFORMATION: primer

<400> SEQUENCE: 47
```
cgttggccga ggcggcctta cttgtacagc tcgtccatg                39

<210> SEQ ID NO 48
<211> LENGTH: 95
<212> TYPE: DNA
<213> ORGANISM: artificial
<220> FEATURE:
<223> OTHER INFORMATION: primer

<400> SEQUENCE: 48
tactcctgca ggatgaagtt ctccaccaat ttgattctag ctattgcagc agcttccgcc    60
gttgtctcag ctgacgttca attgcaagaa tctgg                              95

<210> SEQ ID NO 49
<211> LENGTH: 39
<212> TYPE: DNA
<213> ORGANISM: artificial
<220> FEATURE:
<223> OTHER INFORMATION: primer

<400> SEQUENCE: 49
ctatggccga ggcggcccta ttaacactca cctctgttg                          39

<210> SEQ ID NO 50
<211> LENGTH: 28
<212> TYPE: DNA
<213> ORGANISM: artificial
<220> FEATURE:
<223> OTHER INFORMATION: primer

<400> SEQUENCE: 50
gtaccagctg tgagcaaggg cgaggagc                                       28

<210> SEQ ID NO 51
<211> LENGTH: 39
<212> TYPE: DNA
<213> ORGANISM: artificial
<220> FEATURE:
<223> OTHER INFORMATION: primer

<400> SEQUENCE: 51
cgttggccga ggcggcctta cttgtacagc tcgtccatg                          39

<210> SEQ ID NO 52
<211> LENGTH: 95
<212> TYPE: DNA
<213> ORGANISM: artificial
<220> FEATURE:
<223> OTHER INFORMATION: primer

<400> SEQUENCE: 52
tactcctgca ggatgaagtt ctccaccaat ttgattctag ctattgcagc agcttccgcc    60
gttgtctcag ctgacgttca attgcaagaa tctgg                              95

<210> SEQ ID NO 53
<211> LENGTH: 44
<212> TYPE: DNA
<213> ORGANISM: artificial
<220> FEATURE:
<223> OTHER INFORMATION: primer

<400> SEQUENCE: 53
tcatggccga ggcggcccta ttacttgtca caggactttg gctc                    44

EXPRESSION SEQUENCES

EXPRESSION SEQUENCES

The invention relates to regulatory elements of a *Pichia pastoris* (*P. pastoris*) expression system, and their use in a method to produce a protein of interest (POI).

REFERENCE TO SEQUENCE LISTING

The Sequence Listing submitted Jan. 2, 2018, as a text file named "1023 5-004US2 2018 01 02 Sequence Listing.txt," created on Jan. 2, 2018, and having a size of 13,067 bytes is hereby incorporated by reference pursuant to 37 C.F.R. § 1.52(e)(5).

BACKGROUND

Successful secretion of proteins has been accomplished both with prokaryotic and eukaryotic hosts. The most prominent examples are bacteria like *Escherichia coli*, yeasts like *Saccharomyces cerevisiae*, *Pichia pastoris* or *Hansenula polymorpha*, filamentous fungi like *Aspergillus awamori* or *Trichoderma reesei*, or mammalian cells like e.g. CHO cells. While the secretion of some proteins is readily achieved at high rates, many other proteins are only secreted at comparatively low levels.

The heterologous expression of a gene in a host organism requires a vector allowing stable transformation of the host organism. This vector or expression cassette has to provide the gene with a functional promoter adjacent to the 5' end of the coding sequence. The transcription is thereby regulated and initiated by this promoter sequence.

The secretory pathway typically starts by translocation of transmembrane polypeptides and polypeptides intended for secretion into the lumen of the endoplasmic reticulum (ER). For that purpose, these proteins possess an amino-terminal precursing sequence, also called "leader", comprising or consisting of a signal peptide and an optional secretion leader pro-peptide. The signal peptide typically consists of 13 to 36 rather hydrophobic amino acids. Signal peptides have a common structure: a short, positively charged amino-terminal region (n-region); a central hydrophobic region (h-region); and a more polar carboxy-terminal region (c-region) containing the site that is cleaved by the signal peptidase. On the ER luminal side the signal peptide is cleaved off by a signal peptidase. After successful folding of the nascent polypeptide by ER resident chaperones and foldases, the protein is further directed to exit the ER. This process may be supported by the presence of an N-terminal pro-sequence, as it is present e.g. at the precursor of the *S. cerevisiae* mating factor alfa (MFα). The protein is then transported to the Golgi network and finally to the plasma membrane for secretion into the supernatant. The leader pro-peptide is cleaved off the protein by (presumably) Golgi-resident proteases such as Kex2 protease of *S. cerevisiae*.

As the majority of yeasts do not secrete large amounts of endogenous proteins, and their extracellular proteomes are not extensively characterized so far, the number of available secretion sequences for the use in yeasts is limited. Therefore the fusion of the target protein to the mating factor alfa leader peptide (MFα) from *S. cerevisiae* was employed to drive secretory expression in many yeast species (including *Pichia*, *Kluyveromces*, *Zygosaccharomyces*). Unfortunately the proteolytic processing of the MFα by Kex2 protease often yields heterogeneous N-terminal amino acid residues in the product.

EP324274B1 describes improved expression and secretion of heterologous proteins in yeast employing truncated *S. cerevisiae* alfa-factor leader sequences, EP301669B1 the *Kluyveromyces* alfa-factor leader sequence for secretion of heterologous proteins.

Alternatively, the signal peptides of *S. cerevisiae* phosphatase (PHO5, DK3614), *S. cerevisiae* sucrose invertase (SUC, WO84/01153), and yeast aspartic protease 3 (YAP3, EP792367B1) were used for secretory expression in yeast. EP0438200 (A1) discloses the signal peptide sequence of *S. cerevisiae* SUC2 of for the expression in *P. pastoris*.

U.S. Pat. No. 5,268,273 describes a *P. pastoris* acid phosphatase (PHO1) signal sequence, in most cases weaker than MFα.

U.S. Pat. No. 7,741,075 describes a *P. pastoris* PIR1 secretion signal peptide for recombinant protein expression and *Pichia pastoris* PIR1 and PIR2 anchor domain peptides for recombinant surface display.

Khasa et al. 2011 (Yeast. 28(3):213-26) describe the isolation of *Pichia pastoris* PIR genes and their utilization for cell surface display and recombinant protein secretion, in particular recombinant protein secretion in *P. pastoris*, utilizing the pre-pro signal of PpPir1p protein, without a comparison to MFα.

WO2011073367A1 and Kottmeier et al. 2011 (Applied Microbiology and Biotechnology. 91:1, 133-141) describe a hydrophobin signal sequence which mediates efficient secretion of recombinant proteins in *Pichia pastoris*, in particular the use of the pre-sequence or pro-sequence of *Trichoderma reesei* hydrophobin for secretion of eGFP in *P. pastoris*.

In the course of *P. pastoris* genome sequencing 54 different sequences were listed as predicted signal peptides which include a cleavage site to provide for the secretion of proteins. (De Schutter et al. Nature Biotechnology doi: 10.1038/nbt.1544 2009).

US2011/0021378A1 describes a set of 54 *P. pastoris* genes identified that contain a signal sequence, among them residues 1-21 of SEQ ID 8 as listed in US2011/0021378A1, again including a cleavage site to provide for the secretion of proteins.

EP2258855A1 describes regulatory sequences of a *P. pastoris* derived expression system, wherein a signal and leader sequence of the *P. pastoris* Epx1 protein is used as a 57 amino acid precursing sequence to facilitate expression and secretion of a protein of interest POI. A cleavage site for a signal peptidase is predicted to be following the signal sequence, i.e. between position 20 and 21, indicated as a hyphen in the sequence of the cleavage site: VSA-AP (SEQ ID 6).

It is desirable to provide alternative regulatory elements suitable for expressing a POI in a recombinant eukaryotic host cell, and methods to produce secreted proteins in eukaryotic cells which are simple and efficient, and could preferably lead to a homogeneous N-terminus of the POI.

SUMMARY OF THE INVENTION

The object is solved by the subject matter as claimed.
The invention provides for an isolated nucleic acid encoding a leader, which is selected from the group consisting of
 a) a leader peptide with the amino acid sequence of SEQ ID 10 or a functional variant thereof with one or two point mutations,
 b) a leader peptide with the amino acid sequence selected from the group consisting of SEQ ID 11, 12, 13 and 14,
 c) a signal peptide with the amino acid sequence of SEQ ID 1 or a functional variant thereof with one or two point mutations, preferably excluding SEQ ID 2, and d) a signal peptide with the amino acid sequence selected from the group consisting of SEQ ID 2, 3, 4 and 5, preferably excluding SEQ ID 2.

The invention further provides for a leader, which is selected from the group consisting of a) a leader peptide with the amino acid sequence of SEQ ID 10 or a functional variant thereof with one or two point mutations, b) a leader peptide with the amino acid sequence selected from the group consisting of SEQ ID 11, 12, 13 and 14, c) a signal peptide with the amino acid sequence of SEQ ID 1 or a functional variant thereof with one or two point mutations, preferably excluding SEQ ID 2, and d) a signal peptide with the amino acid sequence selected from the group consisting of SEQ ID 2, 3, 4 and 5, preferably excluding SEQ ID 2.

The specific leader peptide is therefore characterized by a 36 amino acid (aa) leader sequence, wherein the N-terminal 20 aa sequence is a specific signal peptide.

The specific signal peptide is therefore characterized by a 20 aa signal sequence, specifically excluding a C-terminally extended sequence, e.g. a 21 aa sequence that includes a C-terminal extension by an additional amino acid, such as Alanine.

```
SEQ ID 1:
MKXSTNLILAIAAASXVVSA,
``` wherein

X at position 3 is either F or L

X at position 16 is either A or T

For example, the EpxL-A, 20 amino acid (aa) signal peptide, has the amino acid sequence of SEQ ID 1, wherein X at position 3 is L, and X at position 16 is A (SEQ ID 2).

According to a specific example, the EpxL-A, 20 amino acid (aa) signal peptide, has the amino acid sequence of SEQ ID 1, wherein X at position 3 is F, and X at position 16 is A (SEQ ID 3).

Specifically, the invention provides for a signal peptide or a nucleic acid which encodes the signal peptide which has an amino acid sequence selected from the group consisting of SEQ ID 2, 3, 4 and 5.

```
SEQ ID 2:
MKLSTNLILAIAAASAVVSA

SEQ ID 3:
MKFSTNLILAIAAASAVVSA

SEQ ID 4:
MKFSTNLILAIAAASTVVSA

SEQ ID 5:
MKLSTNLILAIAAASTVVSA
```

The amino acid substitutions at position 3 and 16 are indicated bold and underlined.

The nucleic acid molecule encoding the signal peptide according to the invention is herein also called "signal sequence".

The leader according to the invention and as defined above specifically has the amino acid sequence of SEQ ID 10.

```
SEQ ID 10:
MKXSTNLILAIAAASXVVSAAPVAPAEEAANHLHKR,
``` wherein

X at position 3 is either F or L

X at position 16 is either A or T

Specifically, the invention provides a leader or a nucleic acid which encodes the leader which has an amino acid sequence selected from the group consisting of SEQ ID 11, 12, 13 and 14.

```
SEQ ID 11:
MKLSTNLILAIAAASAVVSAAPVAPAEEAANHLHKR

SEQ ID 12:
MKFSTNLILAIAAASAVVSAAPVAPAEEAANHLHKR

SEQ ID 13:
MKFSTNLILAIAAASTVVSAAPVAPAEEAANHLHKR

SEQ ID 14:
MKLSTNLILAIAAASTVVSAAPVAPAEEAANHLHKR
```

The amino acid substitutions at position 3 and 16 are indicated bold and underlined.

For example, the EpxL-KR 36 amino acid (aa) truncated leader, has the amino acid sequence of SEQ ID 10, wherein X at position 3 is L, and X at position 16 is A.

According to a specific example, the EpxL-KR, 36 amino acid (aa) leader peptide, has the amino acid sequence of SEQ ID 10, wherein X at position 3 is F, and X at position 16 is A (SEQ ID 12).

The leader of the present invention with the amino acid sequence of SEQ ID 10, 11, 12, 13 or 14, or a functional variant thereof with one or two point mutations, is herein called the "truncated leader".

Specifically, the nucleic acid encoding the truncated leader comprises or consists of a nucleic acid encoding a signal peptide selected from the group consisting of SEQ ID 2, 3, 4 and 5, preferably excluding SEQ ID 2. Specifically, the nucleic acid encoding the truncated leader comprises or consists of a nucleic acid encoding a leader peptide selected from the group consisting of SEQ ID 11, 12, 13, and 14.

Specifically, the truncated leader comprises or consists of a the signal peptide selected from the group consisting of SEQ ID 2, 3, 4 and 5, preferably excluding SEQ ID 2, or of a leader peptide selected from the group consisting of SEQ ID 11, 12, 13, and 14.

A specifically preferred nucleic acid encodes a signal peptide of the amino acid sequence of SEQ ID 3 or a leader peptide of SEQ ID 12; preferably the nucleic acid sequence encoding the signal peptide or the leader peptide is SEQ ID 16 or SEQ ID 19, respectively. A specifically preferred leader is a signal peptide having the amino acid sequence of SEQ ID 3 or a leader peptide having the amino acid sequence of SEQ ID 12.

Accordingly, a specific embodiment of the invention refers to a leader or a nucleic acid encoding such leader, which is a) a signal peptide with the amino acid sequence of SEQ ID 3, preferably wherein the coding nucleic acid consists of a nucleotide sequence of SEQ ID 16, or a codon optimized variant of SEQ ID 16; or b) a leader peptide with, or comprising or consisting of the amino acid sequence of SEQ ID 12, preferably wherein the coding nucleic acid consists of a nucleotide sequence of SEQ ID 19, or a codon optimized variant of SEQ ID 19.

Specifically, the nucleic acid according to the invention has
a) a nucleotide sequence encoding a signal peptide, selected from the group consisting of SEQ ID 15, 16 and 17, preferably excluding SEQ ID 15, or
b) a nucleotide sequence encoding a leader peptide, selected from the group consisting of SEQ ID 18, 19 and 20, or
c) a nucleotide sequence which is a codon optimized variant of SEQ ID 15, 16, 17, 18, 19 or 20.

A specific nucleic acid of the invention encodes a leader, which is a signal peptide with the amino acid sequence of SEQ ID 3, preferably wherein the nucleic acid consists of a nucleotide sequence of SEQ ID 16, or a codon optimized variant of SEQ ID 16.

A specific nucleic acid of the invention encodes a leader, which is a leader peptide or truncated leader with the amino acid sequence of SEQ ID 12, preferably wherein the nucleic acid consists of a nucleotide sequence of SEQ ID 19, or a codon optimized variant of SEQ ID 19.

SEQ ID 15: nucleotide sequence obtained from *P. pastoris*, strain CBS7435 (CBS-KNAW Fungal Biodiversity Centre, Centraalbureau voor Schimmelcultures, Utrecht, The Netherlands):

ATGAAG<u>C</u>TCTCCAC<u>C</u>AATTTGAT<u>TC</u>TAGCTATTGCAGCAGC<u>T</u>TCC<u>GC</u>CGT

TGTCTCAGCT

SEQ ID 16: nucleotide sequence as used in Example 9, obtained from *P. pastoris* strain CBS7435 by PCR amplification using the primers described in Example 9.

ATGAAGTTCTCTACCAATTTGATTCTAGCTATTGCAGGAGCTTCCGCCGT

TGTCTCAGCT

SEQ ID 17: nucleotide sequence obtained from *P. pastoris*, strain DSMZ70382 (German Collection of Microorganisms and Cell Cultures)

ATGAAG<u>TT</u>CTC<u>T</u>ACCAATTTGAT<u>CT</u>TAGCTATTGCAGCAGC<u>A</u>TCC<u>A</u>C<u>T</u>GT

TGTCTCAGCT

The nucleotides differing in the sequences above are underlined.

SEQ ID 18: nucleotide sequence obtained from *P. pastoris*, strain CBS7435 (CBS-KNAW Fungal Biodiversity Centre, Centraalbureau voor Schimmelcultures, Utrecht, The Netherlands)

ATGAAGCTCTCCACCAATTTGATTCTAGCTATTGCAGCAGCTTCCGCCGT

TGTCTCAGCTGCTCCAGTTGCTCCAGCCGAAGAGGCAGCAAACCACTTGC

ACAAGCGT

SEQ ID 19: nucleotide sequence as used in Example 5, obtained from *P. pastoris* strain CBS7435 by PCR amplification using the primers described in Examples 1 and 5

ATGAAGTTCTCTACCAATTTGATTCTAGCTATTGCAGCAGCTTCCGCCGT

TGTCTCAGCTGCTCCAGTTGCTCCAGCCGAAGAGGCAGCAAACCACTTGC

ACAAGCGT

SEQ ID 20: nucleotide sequence obtained from *P. pastoris*, strain DSMZ70382 (German Collection of Microorganisms and Cell Cultures)

ATGAAGTTCTCTACCAATTTGATCTTAGCTATTGCAGCAGCATCCACTGT

TGTCTCAGCTGCTCCAGTTGCTCCAGCCGAAGAGGCAGCAAACCACTTGC

ACAAGCGT

Specifically the nucleic acid according to the invention is a DNA.

Specifically the leader according to the invention is a polypeptide.

According to a certain aspect, the invention provides for an isolated leader, truncated leader, signal peptide or leader peptide, preferably the leader has an amino acid sequence selected from the group consisting of SEQ ID 1, 2, 3, 4, 5, 10, 11, 12, 13 and 14, preferably excluding SEQ ID 2.

A specifically preferred leader is a peptide consisting of the amino acid sequence of SEQ ID 3 or of SEQ ID 12.

According to another aspect, the invention further provides for expression cassette comprising a nucleic acid encoding a leader operably linked to a nucleic acid sequence encoding a POI, characterized in that the leader is selected from the group consisting of
a) a leader peptide with the amino acid sequence of SEQ ID 10 or a functional variant thereof with one or two point mutations,
b) a leader peptide with the amino acid sequence selected from the group consisting of SEQ ID 11, 12, 13 and 14,
c) a signal peptide with the amino acid sequence of SEQ ID 1 or a functional variant thereof with one or two point mutations, and
d) a signal peptide with the amino acid sequence selected from the group consisting of SEQ ID 2, 3, 4 and 5,
preferably wherein the fusion of the signal peptide consisting of the amino acid sequence SEQ ID 2 with a polypeptide comprising or consisting of one or more immunoglobulin single variable domains is excluded, such as for example a nanobody.

Yet, according to specific examples, the invention provides for the fusion of the leader peptide with the amino acid sequence selected from the group consisting of SEQ ID 11, 12, 13 and 14, or the fusion of the signal peptide with the amino acid sequence selected from the group consisting of SEQ ID 2, 3, 4 and 5 with a POI selected from the group consisting of growth factors, hormones, cytokines, antibodies and antibody fragments, in particular wherein an antibody or antibody fragment is selected from the group consisting of an scFv, minibody, diabody, triabody, tetrabody, Fab, Fc-fusion protein and a full-length antibody such as for example IgG, IgA, IgD, IgM or Ig, preferably a full-length antibody, a scFv or a Fab, specifically including the fusion of the signal peptide consisting of the amino acid sequence SEQ ID 2 with any of such antibodies or antibody fragments, specifically any of a full-length antibody, a scFv or a Fab.

A specifically preferred nucleotide sequence encoding the signal or leader peptide as used in the expression cassette consists of a nucleotide sequence encoding the amino acid sequence of SEQ ID 3 or SEQ ID 12, preferably consists of SEQ ID 16 or SEQ ID 19, or a codon optimized variant of SEQ ID 16 or 19. Such signal or leader peptide is preferably fused to any POI, including any of the antibodies or antibody fragments, specifically including the fusion of the signal peptide or leader peptide consisting of the amino acid sequence SEQ ID 3 or SEQ ID 12 with a polypeptide comprising or consisting of one or more immunoglobulin single variable domains, such as for example a nanobody.

According to another aspect, the invention further provides for an expression cassette comprising a) a nucleotide sequence encoding a signal peptide, selected from the group consisting of SEQ ID 15, 16 and 17, or b) a nucleotide sequence encoding a leader peptide, selected from the group consisting of SEQ ID 18, 19 and 20, or c) a nucleotide sequence which is a codon optimized variant of SEQ ID 15, 16, 17, 18, 19 or 20, preferably wherein the fusion construct of the nucleotide sequence of SEQ ID 15 fused to a nucleotide sequence encoding one or more immunoglobulin single variable domains such as for example a nanobody is excluded.

Yet, according to a specific example, the invention provides for the fusion construct of the nucleotide sequence of SEQ ID 15 fused to a nucleotide sequence encoding an antibody or antibody fragment selected from the group consisting of an scFv, minibody, diabody, triabody, tetrabody, Fab, Fc-fusion protein and a full-length antibody such as for example IgG, IgA, IgD, IgM or IgE, preferably a full-length antibody, a scFv or a Fab.

A specifically preferred nucleotide sequence is SEQ ID 16, encoding the signal peptide of SEQ ID 3.

Another specifically preferred nucleotide sequence is SEQ ID 19, encoding the leader peptide of SEQ ID 12.

Therefore, according to specific examples, the invention provides for the fusion construct of the nucleotide sequence of SEQ ID 16 or 19 fused to a nucleotide sequence encoding any protein of interest, e.g. specifically a POI as described herein, including, but not limited to, any of the antibodies or antibody fragments, specifically including the fusion constructs wherein the POI is a polypeptide comprising or consisting of one or more immunoglobulin single variable domains, such as for example a nanobody.

By the expression cassette according to the invention it was the first time possible to provide for the expression of a POI, and specifically a secreted mature POI, with a correct, native N-terminal amino acid residue, in particular without an additional Alanine at the N-terminus.

Specifically, the POI is selected from therapeutic proteins, including antibodies or fragments thereof, enzymes and peptides, protein antibiotics, toxin fusion proteins, carbohydrate—protein conjugates, structural proteins, regulatory proteins, vaccines and vaccine-like proteins or particles, process enzymes, growth factors, hormones and cytokines, or wherein said POI mediates the production of a host cell metabolite, preferably selected from the group consisting of antibodies or fragments thereof, growth factors, hormones and cytokines.

According to specific examples, the antibody or fragments thereof are selected from the group consisting of an scFv, minibody, diabody, triabody, tetrabody, Fab, Fc-fusion protein and a full-length antibody such as for example IgG, IgA, IgD, IgM or IgE, preferably a full-length antibody, a scFv or a Fab.

Specifically, the expression cassette according to the invention is a fusion of a nucleic acid according to the invention with a nucleic acid encoding a POI and as such is a non-naturally occurring nucleic acid. The invention further provides a fusion protein of a leader according to the invention with a POI and as such is a non-naturally occurring fusion protein.

Therefore, the leader is engineered for the improved production of a POI, e.g. for an increased secretion yield and improved quality such as the correct N-terminus, and employs a leader different from the leaders of the prior art.

The expression cassette according to the invention specifically encodes a leader sequence consisting either of the signal peptide, or the signal peptide prolonged by the pro-sequence consisting of APVAPAEEAANHLHKR (SEQ ID 7), which pro-sequence is part of the native full-length leader of the *P. pastoris* Epx1 protein, i.e. a 16 amino acid sequence identical to amino acids 21-36 of the 57 amino acid sequence of

```
SEQ ID 8:
MKFSTNLILAIAAASTVVSAAPVAPAEEAANHLHKRAYYTDTTKTHTFTE
VVTVYRT.
```

Both leaders, the signal peptide and the truncated leader of the invention, surprisingly turned out to have unexpected improved properties over the leaders of the prior art, e.g.

```
SEQ ID 21:
MKLSTNLILAIAAASAVVSAA,
``` herein also called EpxL-AA (21 amino acids): according to US2011/0021378A1.

Moreover, improved properties could be shown compared to the full-length leader of the *P. pastoris* Epx1 protein as described in EP2258855A1, which is the 57 amino acid sequence of SEQ ID 8 or a variant thereof with a Leucine at position 3.

This was the more surprising, because according to the invention the 20 amino acid signal peptide without a pro-sequence or the truncated leader has a length of only 35% and 63% of the full-length leader, respectively.

The leader of the invention would have specific advantages when fused to a POI, such as an increased secretion of the POI and/or an improved quality such as the correct N-terminus as compared to the fusion with the alpha mating factor (aMF) leader, specifically when the POI is a hormone, a cytokine, an antibody or antibody fragment, e.g. selected from the group consisting of an scFv, minibody, diabody, triabody, tetrabody, Fab, Fc-fusion protein and a full-length antibody such as for example IgG, IgA, IgD, IgM or IgE, preferably a full-length antibody, a scFv or a Fab.

The expression cassette according to the invention explicitly excludes a nucleic acid encoding the native leader of the *P. pastoris* Epx1 protein as described in EP2258855A1 (SEQ ID 8).

The expression cassette according to the invention further explicitly excludes a nucleic acid encoding the leader with the amino acid 1-21 of the full-length leader of the *P. pastoris* Epx1 protein, i.e. SEQ ID 11, as described in US2011/0021378A1.

According to a specific aspect of the invention, the expression cassette is optionally incorporated in an expression construct, such as a vector.

According to further specific aspect of the invention, the expression cassette or the expression construct comprises a promoter operably linked to the nucleic acid encoding the leader.

According to a specific embodiment, the invention provides for a recombinant yeast host cell comprising an expression cassette according to the invention, specifically a yeast host cell line, more specifically a production cell line.

According to a specific aspect of the invention the expression cassette is a vector, or part of a vector.

Preferably the yeast is selected from the genus group consisting of *Pichia, Candida, Torulopsis, Arxula, Hansenula, Ogatea, Yarrowia, Kluyveromyces, Saccharomyces, Komagataella*, preferably a methylotrophic yeast, and specifically preferred *P. pastoris, Komagataella pastoris, K. phaffii*, or *K. pseudopastoris*.

According to another specific embodiment, the invention provides for a method of producing a POI in a yeast host cell, comprising:
providing a host cell of the invention,
cultivating said host cell to express said POI, and
purifying the POI to obtain a preparation of a purified POI.

According to the invention, the expression cassette is preferably employed to facilitate the secretion of recombinant genes in yeast host cells, thereby increasing the yield of secreted products.

Therefore the expression cassette according to the invention provides for the efficient expression and secretion of a POI in a host cell transformed with said expression cassette. In this regard, the expression cassette according to the invention is understood as a yeast expression cassette.

Specifically the POI is a recombinant protein, which term herein always is understood to include both polypeptides and proteins, such as produced by the recombinant host cell. The POI may be a heterologous protein, such as heterologous to yeast, e.g., a protein derived from a higher eukaryote such as human or from a yeast species other than *P. pastoris* or an artificial polypeptide or protein. Alternatively, the POI may be a homologous protein derived from yeast such as e.g. *P. pastoris*, which would, however, not be expressed or not expressed in desirable amounts by a native yeast not transformed with the vector according to the invention, but which would be expressed in desirable amounts, e.g. overexpressed to yield significant amounts of the POI or metabolites by the recombinant yeast host cell according to the invention.

Specifically, the POI has an amino acid sequence with a native N-terminal amino acid sequence. Said POI preferably comprises an amino acid sequence that does not comprise an additional Alanine as N-terminal amino acid residue. Specifically, the POI has no additional N-terminal amino acid residues originating from the leader sequence. This is of particular importance for the quality of recombinant protein production and ease of production.

Specifically said POI is a secreted polypeptide or protein, including soluble, extracellular molecules or membrane-bound molecules.

Specifically, said POI is selected from therapeutic proteins, including antibodies or fragments thereof, enzymes and peptides, protein antibiotics, toxin fusion proteins, carbohydrate—protein conjugates, structural proteins, regulatory proteins, vaccines and vaccine-like proteins or particles, process enzymes, growth factors, hormones and cytokines, or wherein said POI mediates the production of a host cell metabolite. The POI may also be an expression product that mediates the production of a host cell metabolite.

Specifically, the POI is selected from the group consisting of growth factors, hormones, cytokines, antibody and antibody fragments, preferably selected from the group consisting of a full-length antibody, such as for example IgG, IgA, IgD, IgM or IgE, an scFv, minibody, diabody, triabody, tetrabody, Fab and a Fc-fusion protein, preferably a full-length antibody, a scFv or a Fab.

Specifically, the POI comprises an N-terminal amino acid residue other than Alanine. Therefore, there is no signal peptidase cleavage site of VSA-AP (SEQ ID 6) as predicted in the prior art (EP2258855A1).

Specifically, the POI may be a secreted protein, such as a mature protein which could be an active form of a protein or a pro-form.

The method according to the invention preferably provides for cultivation of the host cell in a cell culture, and said POI or metabolite is obtained, e.g. as secreted POI, including membrane-bound or soluble or extracellular proteins or metabolites, which are optionally purified from the cell culture supernatant.

According to a further aspect, the invention provides for the use of the nucleic acid or leader of the invention, in particular the nucleic acid encoding a signal peptide or a truncated leader of the invention, for the secretion of a POI from a host cell and/or to increase the secretion of a POI from a host cell, preferably, wherein at least 60, 65, 70, 75, 80, 85, 90, 95, 98, or 100% of the secreted POI comprises a native N-terminal amino acid sequence,

FIGURES

FIG. 1: promoter sequence pG1: SEQ ID 9.

FIG. 2A: Silver-stained SDS-PAGE of the reduced supernatants of *P. pastoris* secreting pTRP with EpxL-RT or MFα, respectively.

Figure 2B:
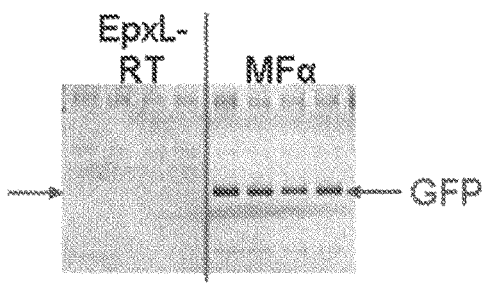

FIG. 2B: Silver-stained SDS-PAGE of the reduced supernatants of *P. pastoris* secreting eGFP with EpxL-RT or MFα.

Figure 2C:
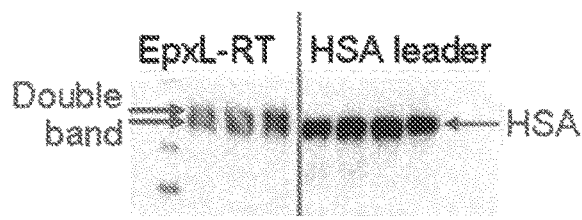

FIG. 2C: anti-HSA Western Blot of the reduced supernatants of *P. pastoris* secreting HSA with EpxL-RT or MFc, respectively.

Figure 3:
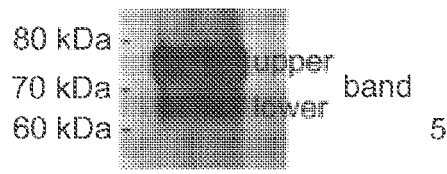

FIG. 3: Coomassie-stained Western Blot of the supernatants of *P. pastoris* secreting HSA with EpxL-RT for N-terminal sequencing.

Figure 4A:
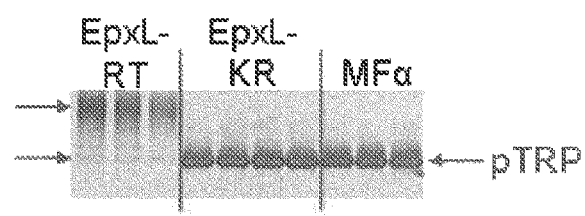

FIG. 4A: Silver-stained SDS-PAGE of the reduced supernatants of *P. pastoris* secreting pTRP with EpxL-RT, EpxL-KR or MFα, respectively.

Figure 4B:
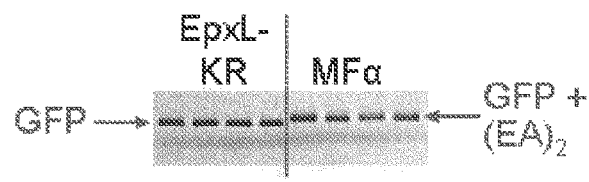

FIG. 4B: Silver-stained SDS-PAGE of the reduced supernatants of *P. pastoris* secreting eGFP with EpxL-KR or MFα, respectively.

Figure 4C:
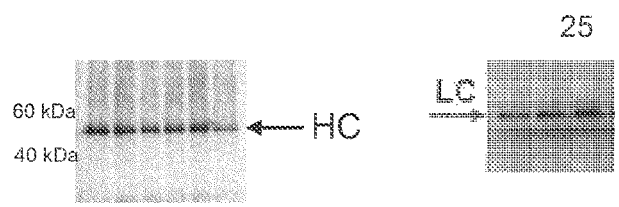

FIG. 4C: Supernatants of *P pastoris* secreting HyHEL heavy chain or HyHEL light chain with EpxL-KR, respectively. HC: Westernblot using anti-IgG gamma chain antibody; LC: SDS-PAGE and silver-stain.

Figure 5A:
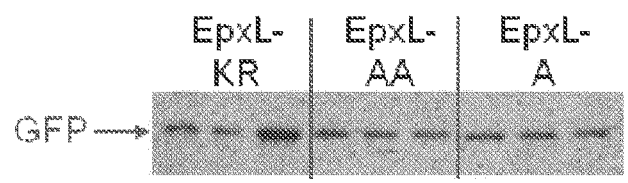

FIG. 5A: Silver-stained SDS-PAGE of the reduced supernatants of *P. pastoris* secreting eGFP with EpxL-KR, EpxL-AA or EpxL-A, respectively.

Figure 5B:
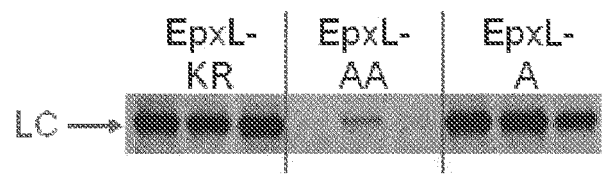

FIG. 5B: Silver-stained SDS-PAGE of the reduced supernatants of *P. pastoris* secreting LC with EpxL-KR, EpxL-AA or EpxL-A, respectively.

Figure 5C:
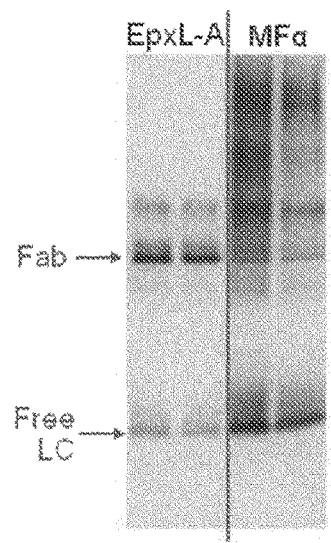

FIG. 5C: Western Blot of the non-reduced supernatants of *P. pastoris* secreting HyHEL Fab under control of pG1 with EpxL-A or MFα, respectively.

Figure 6:
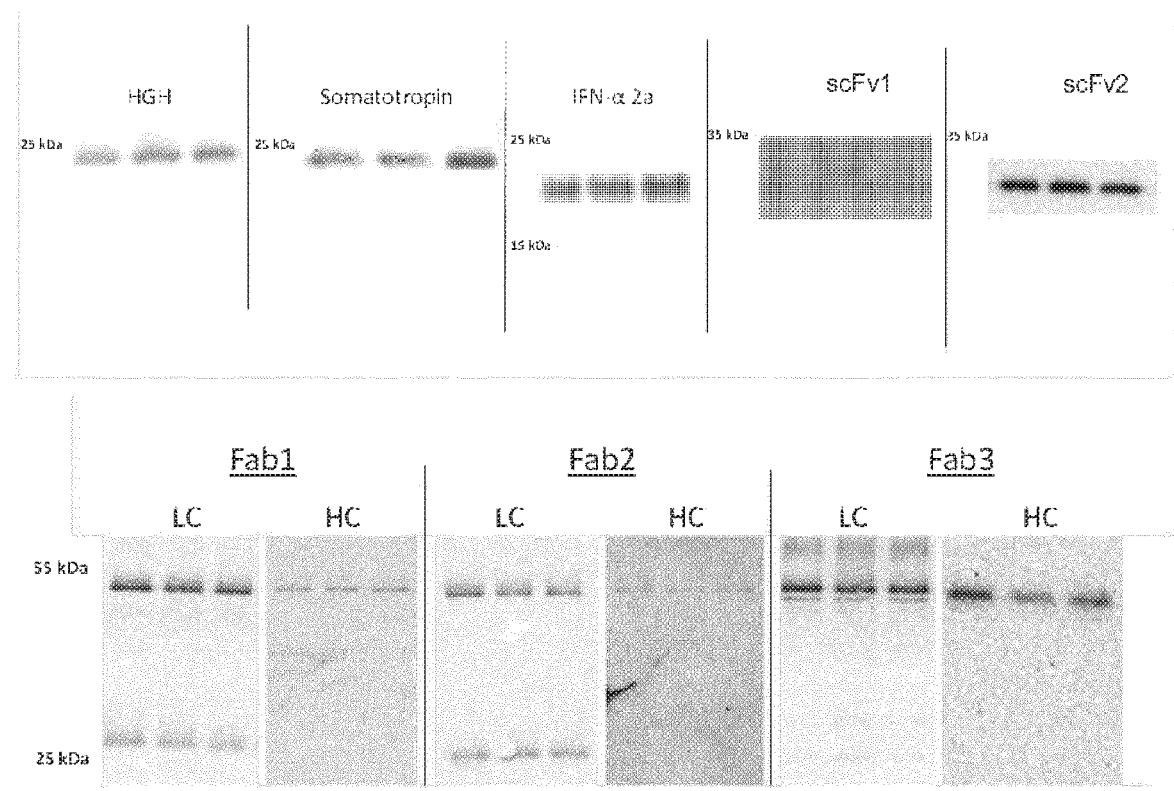

FIG. 6: Western Blot of supernatants of *P. pastoris* secreting human growth hormone (HGH), human somatotropin, interferon alpha2a, 3 different antibody fragments Fab1, Fab2, Fab3, and 2 different single chain Fv antibody fragments scFv1 and scFv2, respectively, under control of pG1 with EpxL-A.

DETAILED DESCRIPTION OF THE INVENTION

Specific terms as used throughout the specification have the following meaning.

The term "cell line" as used herein refers to an established clone of a particular cell type that has acquired the ability to proliferate over a prolonged period of time. The term "host cell line" refers to a cell line as used for expressing an endogenous or recombinant gene or products of a metabolic pathway to produce polypeptides or cell metabolites mediated by such polypeptides. A "production host cell line" or "production cell line" is commonly understood to be a cell line ready-to-use for cultivation in a bioreactor to obtain the product of a production process, such as a POI. The term "yeast host" or "yeast cell line" or "yeast host cell" or "host cell" or "hosts" shall mean any yeast cell, which may be cultivated to produce a POI or a host cell metabolite.

The term "expression" or "expression system" or "expression cassette" refers to nucleic acid molecules containing a desired coding sequence of an expression product such as e.g. a POI and control sequences such as e.g. a promoter in operable linkage, so that hosts transformed or transfected with these sequences are capable of producing the encoded proteins or host cell metabolites. In order to effect transformation, the expression system may be included in a vector; however, the relevant DNA may also be integrated into the host chromosome. Expression may refer to secreted or non-secreted expression products, including polypeptides or metabolites. Specifically the term refers to a host cell and compatible vector under suitable conditions, e.g. for the expression of a protein coded for by foreign DNA carried by the vector and introduced to the host cell.

"Expression constructs" or "vectors" used herein are defined as DNA sequences that are required for the transcription of cloned recombinant nucleotide sequences, i.e. of recombinant genes and the translation of their mRNA in a suitable host organism. Expression vectors comprise the expression cassette and additionally usually comprise an origin for autonomous replication in the host cells or a genome integration site, one or more selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The terms "plasmid" and "vector" as used herein include autonomously replicating nucleotide sequences as well as genome integrating nucleotide sequences.

Specifically the term refers to a vehicle by which a DNA or RNA sequence (e.g. a foreign gene) can be introduced into a host cell, so as to transform the host and promote expression (e.g. transcription and translation) of the introduced sequence. Plasmids are preferred vectors of the invention.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that code for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular polypeptide or protein such as e.g. a POI. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes.

The term "functional variant" as used herein, e.g. with respect to the regulatory sequences according to the invention, such as the signal peptide with the amino acid sequence of SEQ ID 1, or with respect to a leader with the amino acid sequence of SEQ ID 10, shall refer to those variants with one or two point mutations in the amino acid sequence, which have substantially the same signal or leader activity as compared to the unmodified sequences. The functional variants of the nucleic acids of the present invention further encompass codon-optimized sequences, herein also called "codon-optimized variants" which encode any of the signal peptides or leader of the present invention. Such codon optimization of a nucleic acid is understood as the systematic alteration of codons in recombinant DNA to be expressed in a heterologous system to match the pattern of codon usage in the organism used for expression. The intention is specifically to enhance yields of an expressed protein.

It is understood that the terms "signal peptide", "leader" or "truncated leader" as used herein always refers to the specific amino acid of SEQ ID 1 and SEQ ID 10, respectively, and also to functional variants thereof with one or two point mutations.

The term "substantially the same signal or leader activity" as used herein refers to the activity as indicated by substantially the same secretion of a POI into the supernatant by the recombinant host cell; for example a POI level in the supernatant being at least 50%, at least 60%, at least 70%, at least 80%, at least 90%, at least 95%, at least 98% of the POI level in the supernatant as provided by the leader of SEQ ID 1 or SEQ ID 10, respectively.

A point mutation is understood as the engineering of a polynucleotide that results in the expression of an amino acid sequence that differs from the non-engineered amino acid sequence in the substitution or exchange of one or more single (non-consecutive) amino acids for a different amino acid. Preferred functional variants have one or more point mutations at the positions 3 and 16 of SEQ ID 1 and SEQ ID 10, respectively.

Further preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;

Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).
The "positively" charged amino acids are:
Arginine: (Arg, R) polar, positive; and
Lysine: (Lys, K) polar, positive.
The "negatively" charged amino acids are:
Aspartic acid: (Asp, D) polar, negative; and
Glutamic acid: (Glu, E) polar, negative.

The term "isolated" or "isolation" as used herein with respect to a nucleic acid, a POI or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those chemically synthesized. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. Specifically, the term "isolated nucleic acid" according to the invention excludes that the nucleic acid encoding EPX1 protein is linked to a nucleic acid encoding the leader according to the present invention. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

The term "leader" as used herein is understood in the following way. Polynucleotide and nucleic acid coding regions in the expression cassette of the invention can be associated with additional coding regions which encode secretory or signal peptides, which direct the secretion of a POI. Proteins destined towards the secretory pathway have a N-terminal leader sequence which is cleaved from the mature protein once export of the nascent protein chain across the rough endoplasmic reticulum has been initiated. A leader induces an expressed protein to be transported towards or outside the plasma membrane, thereby making it easy to separate and purify the expressed protein. Generally, a membrane protein or a secretory protein which is transported into the periplasm space, the cell membrane or outside of the cell comprises such an N-terminal sequence. Usually, leaders are cleaved from the protein by specialized cellular peptidases after the proteins are transported.

Proteins secreted by eukaryotic cells generally have a leader sequence fused to the N-terminus of the protein, which is cleaved from the complete or "full length" protein to produce a secreted or "mature" form of the protein.

Specific examples of a leader according to the invention are a leader that consists of a signal peptide or a leader consisting of a signal peptide and a prosequence, such as the truncated leader as described herein. The leader consisting of the signal peptide of SEQ ID 1 or the truncated leader of SEQ ID 10, are herein also called regulatory sequences according to the invention.

The term as used herein particularly refers to a control sequence for possible modification of a POI expression. The leader, also called leader peptide, is linked to the N-terminus of a POI amino acid sequence. The nucleic acid encoding the leader is upstream and operably linked to the 5'-terminus of the nucleic acid sequence encoding the POI. Any leader sequence according to the invention that is functional in the host cell of choice may be used.

The term "native N-terminal amino acid residue" or "native N-terminal amino acid sequence" is understood to refer to one or more amino acid(s) of the N-terminal sequence, e.g. the N-terminal amino acid residue of a recited POI, which amino acid residue is considered a correct one when compared to the sequence of a recited POI to be expressed. The native N-terminal amino acid residue, thus, provides for a native N-terminus or N-terminal region of a POI, which is a prerequisite to obtain a correct, complete amino acid sequence, such as to obtain a functional compound without any additional (superfluous) N-terminal amino acid residue(s) foreign to the POI. Typically any wild-type proteins are understood to have a native N-terminal amino acid residue. Also, a recombinant protein may have a native N-terminal amino acid residue as well, which is predefined and exhibits desirable properties of the protein.

Specifically, when the signal peptide or truncated leader of the present invention is attached directly to the native N-terminal amino acid residue of a POI, the liberated protein will contain a natural N-terminal amino acid residue at least to a certain extent, and typically not comprise an N-terminal extension of variable length. The preferred composition of a POI is characterized by a native N-terminal amino acid residue comprises a correct N-terminus, at least to a certain extent which is preferably the majority of the POI molecules, or at least 60, 65, 70, 75, 80, 85, 90, 95, 98, or 100% (w/w) of the POI molecules, without additional amino acid residues at the N-terminus, such as originating from a signal peptide or pro-sequence, or a fragment thereof.

The term "pro-sequence" as used herein shall refer to a precursor amino acid sequence operably linked to the N-terminus of a POI. The pro-sequence may also have a signal sequence operably linked, to the N-terminus of the pro-sequence. Typically the pro-sequence is cleaved from the POI to leave the mature form of the POI.

A specific example of a pro-sequence according to the invention is part of the truncated leader and has the amino acid sequence of

SEQ ID 7:
APVAPAEEAANHLHKR i.e. the truncated pro sequence: amino acids 21-36 of the truncated leader sequence of SEQ ID 10.

The term "operably linked" as used herein refers to the association of nucleotide sequences on a single nucleic acid molecule, e.g. a vector, in a way such that the function of one or more nucleotide sequences is affected by at least one other nucleotide sequence present on said nucleic acid molecule. For example, a promoter is operably linked with a coding sequence of a recombinant gene, when it is capable of effecting the expression of that coding sequence. As a further example, a nucleic acid encoding a signal peptide is operably linked to a nucleic acid sequence encoding a POI, when it is capable of expressing a protein in the secreted form, such as a preform of a mature protein or the mature protein. Specifically such nucleic acids operably linked to each other may be immediately linked, i.e. without further elements or nucleic acid sequences in between the nucleic acid encoding the signal peptide and the nucleic acid sequence encoding a POI.

"Promoter" as used herein refers to a DNA sequence capable of controlling the expression of a coding sequence or functional RNA. Promoter activity may be assessed by its transcriptional efficiency. This may be determined directly by measurement of the amount of mRNA transcription from the promoter, e.g. by Northern Blotting or indirectly by measurement of the amount of gene product expressed from the promoter.

The term "protein of interest (POI)" as used herein refers to a polypeptide or a protein that is produced by means of recombinant technology in a host cell, also called recombinant POI or POI produced by the recombinant host cell. More specifically, the recombinant POI may either be not naturally occurring in the host cell, i.e. a heterologous protein, or else may be native to the host cell, i.e. a homologous protein to the host cell, but is produced, for example, by transformation with a self-replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g. of the promoter or signal sequence. In specific cases the recombinant POI, either the heterologous or homologous POI, is overexpressed by the recombinant host cell, so to obtain high yields of a product. In some cases the term POI as used herein also refers to any metabolite product by the host cell as mediated by the recombinantly expressed protein.

The term "secretion" as used herein refers to translocation of a polypeptide or protein, specifically a POI, across both the plasma membrane and the cell wall of a host plant cell. The secreted POI may be either part of the cell membrane as a membrane-bound protein that is anchored within the cell wall, or released as soluble protein to the cell supernatant.

It is understood that the term "secretion" as used herein with reference to a POI specifically encompasses the expression of a POI in the mature form (including proforms of active proteins or active proteins), either as a membrane-bound POI or as an extracellular POI.

The term "recombinant" as used herein shall mean "being prepared by or the result of genetic engineering". Thus, a "recombinant microorganism" comprises at least one "recombinant nucleic acid". A recombinant microorganism specifically comprises an expression vector or cloning vector, or it has been genetically engineered to contain a recombinant nucleic acid sequence. A "recombinant protein" is produced by expressing a respective recombinant nucleic acid in a host.

Nucleic acid molecules or peptides/polypeptides/proteins of the present invention are preferably recombinant, so to provide for fusions of a leader with a POI. As used herein, "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or expression cassette, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

The term "signal sequence" as used herein shall refer to a nucleic acid encoding a signal peptide, which is usually a short (3-60 amino acids long) peptide chain that directs the transport of a protein. Signal peptides may also be called targeting signals, transit peptides, or localization signals. A signal peptide specifically induces an expressed protein to be transported along the secretory pathway. Generally, a membrane protein or a secretory protein which is transported into the periplasmic space, the cell membrane or outside of the cell comprises such an N-terminal signal sequence. Usually, signal peptides are cleaved from the mature protein by signal peptidase once translocation of the nascent protein chain into endoplasmic reticulum has been accomplished.

A specific example of a signal peptide as used according to the invention is a signal peptide of SEQ ID 1, or a functional variant thereof with one or two point mutations. The signal peptide as used according to the invention typically has inherent characteristics that provide for the cleavage after amino acid Ala20, even without the presence of the cleavage site of SEQ ID 6.

The signal peptide is encoded by a nucleic acid sequence which is typically followed by the nucleic acid sequence encoding a POI, optionally with a pro-sequence downstream the signal sequence and upstream the POI encoding sequence.

The term "substantially pure" or "purified" as used herein shall refer to a preparation comprising at least 50% (w/w), preferably at least 60%, 70%, 80%, 90% or 95% of a compound, such as a nucleic acid molecule or a POI. Purity is measured by methods appropriate for the compound (e.g. chromatographic methods, polyacrylamide gel electrophoresis, HPLC analysis, and the like).

It was surprising to identify and characterize the new isolated nucleic acid encoding the specific signal peptide according to the invention, which signal peptide was found to incorporate an inherent feature that provides for cleavage at the C-terminus independent of the following amino acid residue. This is herein also referred to as an "inherent secretion site" at the C-terminus. Therefore, the amino acid sequence following the signal peptide sequence would have a correct, native N-terminal amino acid sequence once the leader is cleaved off.

Unexpectedly, when using a nucleic acid encoding a signal peptide according to the invention, the cleavage site for signal peptidase known in the art to be located between the signal sequence and the pro-sequence of the native P. pastoris Epx1 leader, i.e. between position 20 and 21, indicated as a hyphen in the sequence of the cleavage site: VSA-AP (SEQ ID 6), could be omitted. Therefore, an improved expression system could be provided for the correct and native N-terminal amino acid residue of a POI, which specifically does not comprise an additional Alanine as N-terminal amino acid residue, at least to a certain extent, e.g. the majority of POI molecules comprise the native N-terminal sequence, up to 100%, as determined by LC-MS.

Therefore, it was the first time possible to use a ready-to-use isolated nucleic acid encoding the 20 amino acid signal peptide. Prior art signal sequences (e.g. of US20110021378A1) always included at least one additional amino acid residue at the C-terminus, which is an Alanine, which could cause an erroneous N-terminus of the protein to be expressed.

Likewise, the truncated leader according to the invention was found to incorporate an inherent feature that provides for cleavage at the C-terminus independent of the following amino acid residue. This is herein also referred to as an "inherent cleavage site" at the C-terminus. Therefore, the amino acid sequence following the C-terminus of the truncated leader or following the C-terminus of the pro-sequence of the truncated leader would have a correct, native N-terminal amino acid sequence once the leader is cleaved off.

The isolated nucleic acids and expression vector of the invention, thus, provide for the expression and secretion of a POI with the native N-terminal amino acid residue. This was the more surprising, because the secretion yields with the 20 amino acid signal peptide were much higher when compared to experiments carried out with the 21 amino acid sequence, i.e. the 20 amino acid signal peptide prolonged by an additional Alanine at the C-terminus as e.g. suggested in US20110021378A1.

Thus, another embodiment of the invention is the use of a nucleic acid or leader peptide according to the invention for the secretion of a POI and/or to increase the secretion of a POI from a host cell, preferably, wherein at least 60, 65, 70, 75, 80, 85, 90, 95, 98, or 100% of the POI comprises a native N-terminal amino acid sequence once the leader according to the invention has been cleaved off. Preferably, the increase in secretion is 1.15, 1.5, 2, 5, 10, 20, 30, 40, 50, 60, 70, 80, 90 or more fold as compared to the known signal peptide SEQ ID 21. Most preferably, the POI is an antibody or fragment or derivative thereof as defined further below.

Further, it was unexpectedly found that a truncated leader sequence could be used, which has a length of only 63% of the native full-length leader of the prior art, thus less than a significant part of the full-length leader sequence of SEQ ID 8. It was surprising to find even increased secretion yields with the truncated leader as compared to experiments carried out with the full-length leader sequence.

According to the invention, the isolated nucleic acids or expression cassette or vector could be used with other conventional regulatory elements or sequences, employed by nature or typically used in recombinant expression systems, e.g. to provide constructs for recombinant protein production at high yields. Examples of regulatory sequences include promoters, operators, and enhancers, ribosomal binding sites, and sequences that control transcription and translation initiation and termination.

To prove the function of the relevant sequences, expression cassettes or vectors may be constructed to drive expression of a POI, and the expressed and/or secreted yield is compared to constructs with conventional regulatory elements. A detailed description of the experimental procedure can be found in the examples below.

The identified sequences were amplified by PCR from *P. pastoris* using specific nucleotide primers, cloned into a yeast expression vector functionally linked to the N-terminus of the POI, or upstream of the POI sequence and transformed into a yeast host cell line, e.g. *P. pastoris*, for high level production of various different POI in the secreted form. To estimate the effect of the regulatory sequences, such as the signal sequence and the truncated leader according to the invention, on the yield of POI, the obtained yeast host cell line according to the invention may be cultured in shake flask experiments and fedbatch or chemostat fermentations in comparison with strains comprising conventional regulatory elements.

By means of the inventive regulatory sequences, in particular sequences encoding the signal peptide or truncated leader and expression vector, the method according to the invention preferably not only provides for an increased production by an enhanced secretion, but also for higher quality of the POI in a yeast host cell and in particular a *P. pastoris* host cell. An increase in secretion of the POI is determined on the basis of a comparison of its secretion yield in the presence of the regulatory sequence, in particular the signal sequence or the truncated leader, that increases protein secretion as compared to prior art elements.

The POI can be any eukaryotic, prokaryotic or synthetic polypeptide. It can be secreted as a mature protein, either as a membrane bound protein or extracellularly expressed protein. The present invention also provides for the recombinant production of functionally equivalent variants, derivatives and biologically active fragments of naturally occurring proteins. Functionally equivalent variants have preferably substantially the same functional characteristics or activity.

A POI referred to herein may be a product homologous to the eukaryotic host cell or heterologous, preferably for therapeutic, prophylactic, diagnostic, analytic or industrial use.

The POI is preferably a heterologous recombinant polypeptide or protein, produced in a yeast cell.

Specifically, the POI is a eukaryotic protein, preferably a mammalian protein.

A POI produced according to the invention may be a multimeric protein, preferably a dimer or tetramer.

According to one aspect of the invention, the POI is a recombinant or heterologous protein, preferably selected from therapeutic proteins, including antibodies or fragments thereof, enzymes and peptides, protein antibiotics, toxin fusion proteins, carbohydrate—protein conjugates, structural proteins, regulatory proteins, vaccines and vaccine-like proteins or particles, process enzymes, growth factors, hormones and cytokines, or a metabolite of a POI.

A specific POI is an antigen binding molecule such as an antibody, or a fragment thereof. Among specific POIs are antibodies such as monoclonal antibodies (mAbs), immunoglobulin (Ig) or immunoglobulin class G (IgG), heavy-chain antibodies (HcAb's), or fragments thereof such as fragment-antigen binding (Fab), Fd, single-chain variable fragment (scFv), or engineered variants thereof such as for example Fv dimers (diabodies), Fv trimers (triabodies), Fv tetramers, or minibodies and single-domain antibodies like VH or VHH or V-NAR.

Further specific POIs are aprotinin, tissue factor pathway inhibitor or other protease inhibitors, and insulin or insulin precursors, insulin analogues, growth hormones, interleukins, tissue plasminogen activator, transforming growth factor a or b, glucagon, glucagon-like peptide 1 (GLP-1), glucagon-like peptide 2 (GLP-2), GRPP, Factor VII, Factor VIII, Factor XIII, platelet-derived growth factor1, serum albumin, enzymes, such as lipases or proteases, or a functional homolog, functional equivalent variant, derivative and biologically active fragment with a similar function as the native protein. The POI may be structurally similar to the native protein and may be derived from the native protein by addition of one or more amino acids to either or both the C- and N-terminal end or the side-chain of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Such modifications are well-known for several of the proteins mentioned above.

A POI can also be selected from substrates, enzymes, inhibitors or cofactors that provide for biochemical reactions in the host cell, with the aim to obtain the product of said biochemical reaction or a cascade of several reactions, e.g. to obtain a metabolite of the host cell. Exemplary products can be vitamins, such as riboflavin, organic acids, and alcohols, which can be obtained with increased yields following the expression of a recombinant protein or a POI according to the invention.

Specifically, the host cell, which expresses a recombinant product according to the invention, can be any yeast cell suitable for recombinant expression of a POI.

Preferred host cells are selected from the genus *Pichia, Candida, Torulopsis, Arxula, Hansenula, Ogatea, Yarrowia, Kluyveromyces, Saccharomyces* or *Komagataella*, and preferably a methylotrophic yeast, and specifically preferred *P. pastoris, Komagataella pastoris, K. phaffii,* or *K. pseudopastoris*.

Examples of preferred host cells according to the invention include but are not limited to the *Pichia* genus, such as *P. pastoris,* or *P. methanolica* or the *Komagataella* genus, such as *K. pastoris, K. pseudopastoris* or *K. phaffii*.

Newer literature divides and renames *Pichia pastoris* into *Komagataella pastoris, Komagataella phaffii* and *Komagataella pseudopastoris*. Herein *Pichia pastoris* is used synonymously for all, *Komagataella pastoris, Komagataella phaffii* and *Komagataella pseudopastoris*.

Examples of the *P. pastoris* strains include CBS 704 (=NRRL Y-1603=DSMZ 70382), CBS 2612 (=NRRL Y-7556), CBS 7435 (=NRRL Y-11430), CBS 9173-9189 (CBS strains: CBS-KNAW Fungal Biodiversity Centre, Centraalbureau voor Schimmelcultures, Utrecht, The Netherlands), and DSMZ 70877 (German Collection of Microorganisms and Cell Cultures), but also strains from Invitrogen, such as X-33, GS115, KM71 and SMD1168. All of the strains described above have been successfully used to produce transformants and express heterologous genes.

According to the invention it is preferred to provide a yeast host cell transformed with a vector comprising a promoter sequence operably linked to the signal sequence or the truncated leader according to the invention.

According to a preferred mode of the invention the expression cassette according to the invention comprises a promoter, such as the *P. pastoris* pGAP (glyceraldehyde phosphate dehydrogenase) promoter, pAOX (alcohol oxidase) promoter or SEQ ID 9 (FIG. 1, pG1 promoter), or functional variants thereof. Significant sequence activity may be obtained with only part of such promoter sequences. Specifically, a preferred part of the promoter sequence consists of at least 150 consecutive bases or bp, more preferred at least 200 bp, at least 300 bp, at least 400 bp, at least 500 bp, at least 600 bp, at least 700 bp, at least 800 bp or at least 900 bp. Preferably the 3' end of the promoter region is contained in the preferred part of the promoter sequence.

In a preferred expression system the promoter is an inducible or a constitutive promoter. The promoter can be an endogenous promoter or heterologous to the host cell. A preferred example of an inducible promoter is the pG1 promoter, which is inducible by glucose-limiting conditions and has the nucleotide sequence of SEQ ID 9.

A specific host cell according to the invention contains heterologous or recombinant promoter sequences, which may be derived from a strain different from the production host, such as from another yeast strain, such as *S. cerevisiae* strain. In another specific embodiment the host cell according to the invention comprises a recombinant expression construct according to the invention comprising the promoter originating from the same genus, species or strain as the host cell.

The promoter may be any DNA sequence which shows transcriptional activity in the host cell and may be derived from genes encoding proteins either homologous or heterologous to the host. The promoter is preferably derived from a gene encoding a protein homologous to the host cell.

For example, a promoter according to the invention may be derived from yeast, such as a *S. cerevisiae* strain. Yet, a specifically preferred embodiment employs a promoter originating from *P. pastoris* for use in a method to produce a recombinant POI in a *P. pastoris* producer host cell line. The homologous origin of the nucleotide sequence facilitates its incorporation into the host cell of the same genus or species, thus enabling stable production of a POI, possibly with increased yields in industrial manufacturing processes. Also, functionally active variants of the promoter from other suitable yeasts or other fungi or from other organisms such as vertebrates or plants can be used.

Further suitable promoter sequences for use with yeast host cells may include but are not limited to promoters obtained from genes that code for metabolic enzymes which are known to be present at high concentration in the cell, e.g. glycolytic enzymes like triosephosphate isomerase (TPI), phosphoglycerate kinase (PGK), glyceraldehyde-3-phosphate dehydrogenase (GAPDH), alcohol oxidase (AOX), lactase (LAC) and galactosidase (GAL).

Preferred examples of suitable promoters are the yeast promoters, which contains a DNA sequence that functions as a promoter for gene transcription in yeast cells. Preferred examples are *S. cerevisiae* Mal, TPI, CUP, ADH or PGK promoters, or the *P. pastoris* glucose-6-phosphate isomerase promoter (PPGI), the 3-phosphoglycerate kinase promoter (PPGK) or glycerol aldehyde phosphate dehydrogenase promoter PGAP, the alcohol oxidase promoter (PAOX), formaldehyde dehydrogenase promoter (PFLD), isocitrate lyase promoter (PICL), translation elongation factor promoter (PTEF), and the promoters of *P. pastoris* enolase 1 (PENO1), triose phosphate isomerase (PTPI), alpha-ketoisocaproate decarboxylase (PTHI), ribosomal subunit proteins (PRPS2, PRPS7, PRPS31, PRPL1), heat shock protein family members (PSSA1, PHSP90, PKAR2), 6-Phosphogluconate dehydrogenase (PGND1), phosphoglycerate mutase (PGPM1), transketolase (PTKL1), phosphatidylinositol synthase (PPIS1), ferro-02-oxidoreductase (PFET3), high affinity iron permease (PFTR1), repressible alkaline phosphatase (PPHO8), N-myristoyl transferase (PNMT1), pheromone response transcription factor (PMCM1), ubiquitin (PUBI4), single-stranded DNA endonuclease (PRAD2) and the promoter of the major ADP/ATP carrier of the mitochondrial inner membrane (PPET9).

If the POI is a protein homologous to the host cell, i.e. a protein which is naturally occurring in the host cell, the expression of the POI in the host cell may be modulated by the exchange of its native promoter sequence with a promoter sequence heterologous to the host cell or with a promoter sequence homologous to the host cell but different to the native promoter sequence of said POI.

This purpose of introducing a new promoter may be achieved e.g. by transformation of a host cell with a recombinant DNA molecule comprising homologous sequences of the target gene to allow site specific recombination, the promoter sequence and a selective marker suitable for the host cell. The site specific recombination shall take place in order to operably link the promoter sequence with the nucleotide sequence encoding the POI. This results in the expression of the POI from the heterologous promoter sequence instead of from the native promoter sequence.

In a specifically preferred embodiment of the invention the promoter sequence has an increased promoter activity relative to the native promoter sequence of the POI.

According to the invention it is also possible to provide a wildcard vector or expression cassette according to the invention, which comprises a signal sequence or truncated leader according to the invention. Such wildcard vector or expression cassette is ready to incorporate a gene of interest encoding a POI. The wildcard cell line is, thus, a preformed host cell line, which is characterized for its expression capacity. This follows an innovative "wildcard" platform strategy for the generation of producer cell lines, for the POI production, e.g. using site-specific cassette integration or site-specific recombinase-mediated cassette exchange. Such a new host cell facilitates the cloning of a gene of interest (GOI), e.g. into predetermined genomic expression sites in order to get reproducible, highly efficient production cell lines.

According to a preferred embodiment the expression vector according to the invention is a plasmid suitable for integration into the genome of the host cell, in a single copy or in multiple copies per cell. The recombinant nucleotide sequence encoding a POI may also be provided on an autonomously replicating plasmid in a single copy or in multiple copies per cell. The preferred plasmid is a eukaryotic expression vector, preferably a yeast expression vector.

Expression vectors may include but are not limited to cloning vectors, modified cloning vectors and specifically designed plasmids. The preferred expression vector as used in the invention may be any expression vector suitable for expression of a recombinant gene in a host cell and is selected depending on the host organism. The recombinant expression vector may be any vector which is capable of replicating in or integrating into the genome of the host organisms, also called host vector, such as a yeast vector, which carries a DNA construct according to the invention. A preferred yeast expression vector is suitable for expression in yeast selected from the group consisting of methylotrophic yeasts represented by the genera *Hansenula, Ogatea, Pichia, Candida* and *Torulopsis*.

In the present invention, it is preferred to use plasmids derived from pPICZ, pGAPZ, pPIC9, pPICZalfa, pGAPZalfa, pPIC9K, pGAPHis or pPUZZLE as the vector.

According to a preferred embodiment of the present invention, a recombinant construct is obtained by ligating the relevant genes into a vector. These genes can be stably integrated into the host cell genome by transforming the host cell using such vectors. The polypeptides encoded by the genes can be produced using the recombinant host cell line by culturing a transformant, thus obtained in an appropriate medium, isolating the expressed POI from the culture, and purifying it by a method appropriate for the expressed product, in particular to separate the POI from contaminating proteins.

The DNA sequence encoding the POI may also be operably connected to a suitable terminator sequence, for example AOX1 (alcohol oxidase) terminator, CYC1 (cytochrome c) terminator, TEF (translation elongation factor) terminator.

Expression vectors may comprise one or more phenotypic selectable markers, e.g. a gene encoding a protein that confers antibiotic resistance or that supplies an auxotrophic requirement. Yeast vectors commonly contain an origin of replication from a yeast plasmid, an autonomously replicating sequence (ARS), or alternatively, a sequence used for integration into the host genome, a promoter region, sequences for polyadenylation, sequences for transcription termination, and a selectable marker.

The procedures used to ligate the DNA sequences, e.g. coding for the leader sequence and/or the POI, the promoter and the terminator, respectively, and to insert them into suitable vectors containing the information necessary for integration or host replication, are well known to persons skilled in the art, e.g. described by J. Sambrook et al., "Molecular Cloning 2nd ed.", Cold Spring Harbor Laboratory Press (1989).

It will be understood that the vector according to the invention may be constructed either by first preparing a DNA construct containing the entire DNA sequence of the required elements of the vector and inserting this construct into a suitable expression vector, or by sequentially inserting DNA fragments containing genetic information for the individual elements, such as the signal, leader or POI followed by ligation. Alternatively, the individual elements of the expression cassette can also fused by PCR.

Also multicloning vectors, which are vectors having a multicloning site, can be used according to the invention, wherein a desired gene can be incorporated at a multicloning site to provide an expression vector. In expression vectors, the promoter is placed upstream of the gene of the leader sequence and the POI and regulates the expression of the gene. In the case of multicloning vectors, because the gene of the leader sequence and the POI is introduced at the multicloning site, the promoter is placed upstream of the multicloning site. The gene of leader sequence can be fused to the gene of the POI either during PCR reaction or synthetic preparation, or the gene of the leader sequence can be provided in the vector or expression cassette and the gene of the POI can be introduced by standard cloning procedures.

The expression vector or cassette and DNA construct as provided according to the invention may be prepared synthetically by established standard methods, e.g. the phosphoramidite method. The DNA construct may also be of genomic or cDNA origin, for instance obtained by preparing a genomic or cDNA library and screening for DNA sequences coding for all or part of the polypeptide of the invention by hybridization using synthetic oligonucleotide probes in accordance with standard techniques (Sambrook et al., Molecular Cloning: A Laboratory Manual, Cold Spring Harbor, 1989). Finally, the DNA construct may be of mixed synthetic and genomic, mixed synthetic and cDNA or mixed genomic and cDNA origin prepared by annealing fragments of synthetic, genomic or cDNA origin, as appropriate, the fragments corresponding to various parts of the entire DNA construct, in accordance with standard techniques.

It is obvious to those skilled in the art, that the DNA sequences encoding the leader and/or the POI may be optimized for the codon usage preference of the host organism, according to state of the art algorithms and techniques (e.g. as provided by commercial suppliers such as for example GeneArt, GeneCust, GenScript or DNA2.0)

In another preferred embodiment, the yeast expression vector or cassette is able to stably integrate in the yeast genome, e.g. by homologous recombination.

In a preferred aspect the invention relates to such a method, wherein the expression vector or cassette comprises a leader sequence effective to cause secretion of a mature POI by the transformed host cell.

The signal sequence or the truncated leader according to the invention can be fused to the nucleotide sequence encoding a POI intended for recombinant expression by conventional cloning techniques known to a skilled person. In preferred embodiments, the nucleotide sequence of a POI is fused to the nucleotide sequence of secretion leader, thus, the signal sequence or the truncated leader is targeting the protein to the secretory pathway where the leader is cleaved and the protein released in the medium.

A transformant host cell according to the invention obtained by transforming the cell with the expression vector or cassette according to the invention may preferably first be cultivated at conditions to grow efficiently to a large cell number without the burden of expressing the POI. When the cell line is prepared for the POI expression, cultivation techniques are chosen to produce the expression product.

The differential fermentation strategies would distinguish between a growth phase and a production phase. Growth and/or production can suitably take place in batch mode, fed-batch mode or continuous mode. Any suitable bioreactor can be used, including batch, fed-batch, continuous, stirred tank reactor, or airlift reactor.

It is advantageous to provide for the fermentation process on a pilot or industrial scale. The industrial process scale would preferably employ volumina of at least 10 L, specifically at least 50 L, preferably at least 1 m$^3$, preferably at least 10 m$^3$, most preferably at least 100 m$^3$.

Production conditions in industrial scale are preferred, which refer to e.g. fed batch cultivation in reactor volumes of 100 L to 10 m$^3$ or larger, employing typical process times of several days, or continuous processes in fermenter volumes of appr. 50-1000 L or larger, with dilution rates of approximately 0.02-0.4 h$^{-1}$.

The suitable cultivation techniques may encompass cultivation in a bioreactor starting with a batch phase, followed by a short exponential fed batch phase at high specific growth rate, further followed by a fed batch phase at a lower specific growth rate. Another suitable cultivation technique may encompass a batch phase followed by a continuous cultivation phase at a lower dilution rate. A preferred embodiment of the invention includes a batch culture to provide biomass followed by a fed-batch culture for high yields POI production.

It is preferred to cultivate the host cell line according to the invention in a bioreactor under growth conditions to obtain a cell density of at least 1 g/L cell dry weight, more preferably at least 10 g/L cell dry weight, preferably at least 20 g/L cell dry weight. It is advantageous to provide for such yields of biomass production on a pilot or industrial scale.

It is understood that the methods disclosed herein may further include cultivating said recombinant host cells under conditions permitting the expression of the POI. A membrane-bound or soluble, recombinantly produced POI or a host cell metabolite can then be isolated from the cell culture medium and further purified by techniques well known to a person skilled in the art.

Several different approaches for the POI expression and secretion by the host cell are preferred. Proteins are expressed, processed and secreted by transforming the eukaryotic organism with an expression vector or cassette according to the invention harbouring DNA encoding the desired protein, preparing a culture of the transformed organism, growing the culture and recovering the protein from the culture medium, e.g. concentrating and enriching the protein in a fraction of the cell culture, or purifying the protein so to obtain a substantially pure preparation. Also host cells deleted for one or more of the major contaminating host cell proteins (e.g. as described by Heiss et al. 2012; Appl Microbiol Biotechnol. doi: 10.1007/s00253-012-4260-4) can be applied to facilitate purification of the POI.

As isolation and purification methods for obtaining a recombinant polypeptide or protein product, methods, such as methods utilizing difference in solubility, such as salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used.

The highly purified product is essentially free from contaminating proteins, and preferably has a purity of at least 90%, more preferred at least 95%, or even at least 98%, up to 100%. The purified products may be obtained by purification of the cell culture supernatant or else from cellular debris.

The isolated and purified POI can be identified by conventional methods such as Western blotting or assay of its activity. The structure of the purified compound can be defined by amino acid analysis, amino-terminal analysis, primary structure analysis, and the like. It is preferred that the compound is obtainable in large amounts and in a high purity level, thus meeting the necessary requirements for being used as an active ingredient in pharmaceutical compositions.

The preferred host cell line according to the invention maintains the integration of the regulatory sequences according to the invention and POI gene, and the expression level remains high, e.g. at least at a µg/L level, even after about 20 generations of cultivation, preferably at least 30 generations, more preferably at least 40 generations, most preferred of at least 50 generations. The recombinant host cell is surprisingly stable, which is a great advantage when used for industrial scale protein production.

The present invention is described in further detail in the following examples, which are not in any way intended to limit the scope of the invention as claimed.

EXAMPLES

Example 1: Construction of a *P. pastoris* Host Cell Line for the Expression of Recombinant Proteins Using the *P. pastoris* Epx1 Native Leader (SEQ ID 8) for Secretion 1a): Construction of an Expression Vector Containing the *P. pastoris* Epx1 Native Leader (Signal Sequence and Pro-Sequence; SEQ ID 8, EpxL-RT, the "Percussing Sequence")

The identification of the natively secreted protein Epx1 in *P. pastoris* and the identification of the putative secretion leader sequence EpxL-RT (consisting of the Epx1 signal sequence and pro-sequence up to the experimentally determined N-terminus of the mature Epx1 protein) was described in EP2258855. As the last amino acids preceding the experimentally verified N-terminus of mature Epx1 were Arg-Thr (RT), the putative secretion leader sequence was termed EpxL-RT.

To generate an expression vector using the secretion leader sequence of the *P. pastoris* Epx1 protein for secretion of a POI, the respective sequence (SEQ ID 8) was cloned in frame with the PGAP promoter (glyceraldehyde 3-phosphate dehydrogenase promoter) of the pPM2_pGAP expression vector. The pPM2_pGAP expression vector is a derivative of the pPuzzle_zeoR_AOXTT vector backbone described in WO2008/128701A2, consisting of the pUC19 bacterial origin of replication, the *P. pastoris* glycerol aldehyde phosphate dehydrogenase promoter, the *S. cerevisiae* CYC1 transcription terminator, and the Zeocin antibiotic resistance cassette.

The Epx1 secretion leader sequence was amplified by PCR from *P. pastoris* genomic DNA using the oligonucleotide primers (Table 1).

TABLE 1

Oligonucleotide primer for PCR amplification of
the precursing sequence of the *P. pastoris* Epx1
protein EpxL-RT (restriction sites are underlined)

| EpxL forw | SbfI | SEQ ID 22<br>TATA<u>CCTGCAGG</u>ATGAAGTTCTCTACCAATTTGATC |
|---|---|---|
| EpxL back | NsiI | SEQ ID 23<br>GAAG<u>ATGCAT</u>CGTACGGTAGACAGTGACAAC |

Subsequently, the PCR product (189 bp) was digested by the restriction enzymes SbfI and NsiI; and ligated into a pPM2_pGAP vector that has been linearized by SbfI and treated with calf intestine phosphatase (CIP). As NsiI and SbfI produce overlapping ends, the resulting construct pPM2_pGAPxLRT has a single SbfI site directly before the start codon of the EpxL-RT sequence. Correct integration was verified by digestion of the resulting plasmids with SbfI and AscI.

1 b) Construction of a *P. pastoris* Strain Secreting Recombinant Porcine Trypsinogen Using the pPM2 pGAPxLRT Vector.

For expression of recombinant porcine trypsinogen (rpTRP) a codon-optimized artificial gene was synthesized (Geneart, Germany). Sites for the restriction enzymes Pfl23II and SfiI, flanking the open reading frame were added during PCR amplification using the delivered plasmid as template, primers are shown in Table 2.1. The PCR product was digested with Pfl23II and SfiI, and cloned into a Pfl23II, SfiI and CIP treated plasmid pPM2_pGAPxLRT (Example 1a). The ligated plasmid was transformed into *E. coli* TOP10 (Invitrogen) and plated on Zeocin containing LB-agar. Restriction endonuclease analysis was performed to confirm the correct identity of the plasmid pPM2_pGAPxLRT_rpTRP.

TABLE 2.1

Oligonucleotide primer for PCR amplification
of the gene for porcine trypsinogen

| EpxL-RT-<br>pTRP forw | Pfl23II<br>(BsiWI) | SEQ ID 24<br>ATAC<u>CGTACG</u>ACTGACGACGACGACAAG |
|---|---|---|
| pTRP back | SfiI | SEQ ID 25<br>TTTT<u>GGCCGAGGCGGCC</u>TTTCAGTTAGCAGCGATAGTTTG |

1c) Construction of a *P. pastoris* Strain Overexpressing Recombinant Human Serum Albumin or Enhanced Green Fluorescent Protein the PPM2 pGAPxLRT Vector.

The genes encoding human serum albumin (HSA) or enhanced green fluorescent protein (eGFP) were amplified by PCR from vectors described in Stadlmayr et al. (2010, J Biotechnol. 150: 519-529) using the primers shown in Table 2.2. The PCR products were digested with AccI and SfiI, and cloned into the AccI and SfiI treated plasmid pPM2_pGAPxLRT (Example 1a). The ligated plasmid was transformed into *E. coli* TOP10 (Invitrogen) and plated on Zeocin containing LB-agar. After sequence verification, the vectors pPM2_pGAPxLRT-HSA and pPM2_pGAPxLRT-eGFP were linearized in the promoter region and transformed into *P. pastoris*. For HSA, the construct using the native HSA leader described in Stadlmayr et al. 2010 was used as reference, while eGFP was cloned after the *S. cerevisiae* MFα leader as control.

TABLE 2.2

Oligonucleotide primers for PCR amplification of
HSA and eGFP fused to EpxL-RT and eGFP
fused to *S. cerevisiae* MFα leader

| EpxL-RT-<br>HSA forw | AccI | SEQ ID 26<br>AGGC<u>GTCTAC</u>CGAACTGATGCACACAAGAGTGAGGTT |
|---|---|---|
| HSA back | SfiI | SEQ ID 27<br>GAGT<u>GGCCGAGGCGGCC</u>TTATAAGCCTAAGGCAGCTTGA |
| EpxL-RT-<br>eGFP forw | AccI | SEQ ID 28<br>ATTT<u>GTCTAC</u>CGAACTGTGAGCAAGGGCGAGGAGC |
| eGFP back | SfiI | SEQ ID 29<br>CGTT<u>GGCCGAGGCGGCC</u>TTACTTGTACAGCTCGTCCATG |

Example 2: Cultivation of a *P. pastoris* Host Cell Line for the Expression of Recombinant Secretory Proteins and Product Analysis All plasmids were linearized in their respective promoter region or the AOX-TT integration region prior to electro-transformation into *P. pastoris*. Positive transformants were selected on YPD agar plates containing yeast extract (10 g/L), peptone (20 g/L), glucose (20 g/L) and Zeocin.

2a) Culturing Transformed *P. pastoris* Strains Expressing Recombinant Secretory Proteins in Small Scale Cultures 5 mL YP-medium (10 g/L yeast extract, 20 g/L peptone) containing 10 g/L glycerol were inoculated with a single colony of *P. pastoris* strains from Examples 1 b, 5, 7, or 9 and grown overnight at 28° C. Aliquots of these cultures (corresponding to a final $OD_{600}$ of 0.1) were transferred to 10 mL of expression culture medium (media composition is given below for each recombinant protein) supplemented with 20 g/L glucose and incubated for 48 h at 28° C. at 170 rpm in 100 mL Erlenmeyer flasks. Alternatively, 2 mL of expression culture medium was used for cultivation in 24 deep well plates. Glucose (10 g/L) was added repeatedly every 12 h, before cells were harvested by centrifugation at 2500×g for 10 min at room temperature and prepared for analysis. For pG1-driven expression, glucose-limiting growth conditions were achieved by using glucose feed beads (Kuhner, CH), which slowly release glucose over time according to the equation (Glucose)=$1.63*t^{0.74}$ [mg/Disc], instead of glucose supplementation. For 10 mL of main culture 2 feed beads were used. Biomass was determined by measuring the cell weight after centrifugation of 1 mL cell suspension, while determination of the recombinant secreted protein in the supernatant is described in the following Examples 2b-2e.

Expression Culture Media were as Follows:

For porcine trypsinogen: per liter: 10 g yeast extract, 10 g pea-peptone, 10.2 g $(NH_4)_2PO_4$, 1.24 g KCl, 0.1 g $CaCl_2$, pH 5.0 adjusted with HCl For HSA: per liter: 22 g citric acid, 3.15 g $(NH_4)_2HPO_4$, 0.027 g $CaCl_2*2H_2O$, 0.9 g KCl, 0.5 g $MgSO_4*7H_2O$, 2 ml 500× biotin and 1.47 mL trace salts stock solution [per liter: 6 g $CuSO_4*5H_2O$, 0.08 g NaI, 3 g $MnSO_4*H_2O$, 0.2 g $Na_2MoO_4*2H_2O$, 0.02 g $H_3BO_3$, 0.5 g $COCl_2$, 20 g $ZnCl_2$, 5 g $FeSO_4*7H_2O$ and 5 mL $H_2SO_4$]; pH set to 6 with 5M KOH; sterilized by filtration.

For eGFP and for antibody fragments (e.g. Fab): per liter: 10 g yeast extract, 10 g peptone, 100 mM potassium phosphate buffer pH 6.0, 13.4 g yeast nitrogen base with ammonium sulfate, 0.4 mg biotin 2b) Quantification of Trypsin

*P. pastoris* culture supernatant was desalted using small pre-packed size exclusion chromatography columns (Disposable PD-10 Desalting Columns 17-0851-01; GEHealthcare). 2.5 mL of supernatant were applied to the column and eluted with 3.5 mL of elution buffer (1 mM HCl). After elution 70 µL of 2 M $CaCl_2$ solution was added.

To convert inactive trypsinogen to the active trypsin 300 µL of the desalted supernatant (+$CaCl_2$) were mixed with 690 µL of activation buffer (50 mM TRIS/HCl pH 8.6; 40 mM $CaCl_2$ and 0.15 g/L Enterokinase, Sigma; E0632) and incubated for two hours at 37° C.

165 µL of the activation mixture were mixed with 1000 µL of TAME-solution, containing 446 mg/L Na-p-Tosyl-L-arginine-methyl-ester-hydrochloride (TAME; Sigma; T4626) dissolved in dilution buffer (50 mM TRIS/HCl pH 8.1; 40 mM $CaCl_2$) and an absorption kinetic at 247 nm was measured in a spectrophotometer over a time period of 5 min at 30° C. If necessary, activated trypsin solution was diluted with dilution buffer to hit the linear range ($\Delta A247/min<0.3$) of this method. A trypsin concentration of 1 g/L corresponds to $\Delta A247/min=0.101$.

2c) Quantification of HSA by ELISA

For the quantification of HSA in *P. pastoris* supernatants, the Human Albumin ELISA Quantitation Set (Cat. No. E80-129, Bethyl Laboratories, Tex., USA) was used. The HSA standard was used with a starting concentration of 400 ng/mL. Supernatant samples were diluted accordingly.

2d) SDS-PAGE & Western Blot Analysis

For protein gel analysis the NuPAGE® Novex® Bis-Tris system was used, using 12% Bis-Tris or 4-12% Bis-Tris gels and MOPS running buffer (all Invitrogen). After electrophoresis, the proteins were either visualized by silver staining or transferred to a nitrocellulose membrane for Western blot analysis. Therefore, the proteins were electroblotted onto a nitrocellulose membrane using the XCell II™ Blot Module for wet (tank) transfer (Invitrogen) according to the manufacturer's instructions. After blocking, the Western Blots were probed with the following antibodies: For HSA: anti-human serum albumin-horse radish peroxidase (HRP) conjugate, Bethyl A80-129P (1:50,000); For IgG light chain: anti-human kappa light chains (bound and free)—alkaline phosphatase (AP) conjugated antibody, Sigma A3813 (1:5, 000); For IgG heavy chain: anti-human-IgG (γ-chain specific)-antibody produced in goat, Sigma 13382 (1:5,000) and anti-goat AP conjugate (1:20,000).

Detection was performed with the colorimetric AP detection kit (BioRad) based on the NBT/BCIP system for AP-conjugates, and the chemiluminescent Super Signal West Chemiluminescent Substrate (Thermo Scientific) for HRP-conjugates.

2e) Quantification of Fab by ELISA

Quantification of intact Fab was done by ELISA using anti-human IgG antibody (Abcam ab7497) as coating antibody (1:1,000), and a goat anti-Human Kappa Light Chains (Bound and Free)—alkaline phosphatase conjugated antibody (Sigma A3813) as detection antibody (1:1,000). Human Fab/Kappa, IgG fragment (Bethyl P80-115) was used as standard with a starting concentration of 50 ng/mL. Supernatant samples were diluted accordingly. Detection was done with pNPP substrate (Sigma S0942). Coating-, Dilution- and Washing buffer were based on PBS (2 mM $KH_2PO_4$, 10 mM $Na_2HPO_4.2 H_2O$, 2.7 mM g KCl, 8 mM NaCl, pH 7.4) and completed with BSA (1% (w/v)) and/or Tween20 (0.1% (v/v)) accordingly.

Example 3: Expression of Recombinant Proteins by a *P. pastoris* Host Cell Line Using the *P. pastoris* Epx1 Precussing Sequence (EpxL-RT, SEQ ID 8) for Secretion 3a) Analysis of *P. pastoris* Overexpressing Recombinant Porcine Trypsinogen Using EpxL-RT for Secretion

*P. pastoris* expressing pTRP using the EpxL-RT sequence for secretion were cultivated as described in Example 2a and analysed using trypsin activity assay as described in Example 2b and SDS-PAGE described in Example 2d. *P. pastoris* expressing pTRP using MFα for secretion were used as a reference.

Unexpectedly, pTRP expression using the EpxL-RT secretion leader led to a protein smear of approximately 30 kDa (FIG. 2.1, left side), whereas MFα led to secreted pTRP of correct size (25 kDa; FIG. 2.1, right side). Parts of secreted pTRP with EpxL-RT also led to correct size pTRP, albeit to a lesser extent. The amounts of pTRP secreted with EpxL-RT were less than 50% of the amount secreted using MFα (Table 3, measured by trypsin activity assay as described in Example 2b). The smeared band probably represents an EpxL-RT-pTRP fusion protein, which appears due to incorrect processing (cleavage) of the EpxL-RT sequence.

TABLE 3

Relative secretion levels of pTRP normalized to alfaMF

| Leader | Relative mean pTRP secretion ± SEM |
|---|---|
| EpxL-RT | 0.48 ± 0.02 |
| MFα | 1.00 ± 0.05 |

3b) Analysis of *P. pastoris* Overexpressing Recombinant eGFP Using EpxL-RT for Secretion

*P. pastoris* expressing eGFP using the EpxL-RT sequence for secretion were cultivated as described in Example 2a and analysed using SDS-PAGE and Western Blot (Example 2d). Apparently, native EpxL-RT failed to secrete eGFP completely (FIG. 2.2, left part), in contrast to MFα (FIG. 2.2, right part). Intracellularly, eGFP still attached to parts of the EpxL-RT sequence could be observed, thus ruling out defects in protein expression (not shown).

3c) Analysis of *P. pastoris* Overexpressing Recombinant Human Serum Albumin Using EpxL-RT for Secretion

*P. pastoris* expressing HSA using the EpxL-RT sequence for secretion were cultivated as described in Example 2a and analysed using HSA ELISA (Example 2c) and Western Blot (Example 2d). *P. pastoris* expressing HSA using the native HSA leader for secretion were used as a reference (Kobayashi. 2006. Biologicals. 34(1):55-9.).

12 individual clones of each construct were analysed for their secretion behaviour after 48 h shake-flask cultivation in synthetic-screening-medium. The supernatant was qualitatively examined by reducing SDS-PAGE and subsequent Western Blotting, using anti-HSA antibody for detection of HSA. A distinct double band pattern was visible for HSA secreted by EpxL-RT (FIG. 2.3, left side). In comparison with HSA secreted by its native leader (FIG. 2.3, right side) and purified HSA (not shown), the lower band was correctly processed HSA. The upper band was unexpected, but due to its slightly bigger molecular weight, it may represent an EpxL-RT-HSA fusion protein due to incorrectly processed EpxL-RT. Based on band intensity (as analysed by ImageJ) 40-60% of total secreted HSA was present as the incorrect higher molecular weight form.

Summary: When using the EpxL-RT sequence for secretion, a smear or double band pattern is visible for the secreted recombinant protein, which is indicative of incorrect or no processing of the long leader EpxL-RT. This feature renders EpxL-RT corresponding to the full length Epx1 leader sequence of EP2258855A1 unsuitable and not useful for recombinant protein secretion.

Example 4: Identification of the N-Terminus of Higher Molecular Weight Band of HSA Expression Cultures The N-terminus of HSA expressed as described in Example 3c above using EpxL-RT was then further analysed by N-terminal sequencing.

Therefore, 500 μL of respective supernatant was loaded onto a centrifugal filter for concentrating the protein (Amicon Ultra-0.5 mL 10 kDa centrifugal filter, Millipore, UFC5010), centrifuged for 5 min and 15 μL sample were recovered by reverse spin.

Thereafter, samples were separated by a 4-12% Bis-Tris NuPAGE gel and a Western blot with borate buffer (per liter: 3.09 g Borate [50 mM], 100 mL MeOH at pH 9 set with 1M NaOH) was performed for 2 h at 25 V using a PVDF (polyvinylidene fluoride) membrane. Prior to blotting, the gel was incubated in borate buffer for 10 min, whereas the membrane was dipped into methanol for 30 sec followed by 3 min in borate buffer.

After blotting, the membrane was stained for 3 min with Coomassie (0.1% [w/v]R250, MeOH [40% v/v], acetic acid [10% v/v]), followed by destaining (MeOH [40% v/v], acetic acid [10% v/v]). The membrane was rinsed with ddH$_2$O and the upper and lower bands (FIG. 3) were cut out and sent for N-terminal EDMAN sequencing. For the lower band, D was determined as the N-terminal amino acid, conclusively with the first amino acid of HSA (N-terminus of HSA, SEQ ID 30: DAHKSEV), while for the upper band AYYT (SEQ ID 31) was determined as N-terminus of the secreted protein. These amino acids are part of the EpxL-RT sequence (SEQ ID 8), leaving an unwanted 21 amino acid overhang on HSA. The sequence of EpxL-RT preceding AYYT (SEQ ID 23) is KR, which might be part of a dibasic Lys-Arg peptidase cleavage motif. Processing of dibasic Lys-Arg motifs by proteases such as Kex2 depends not only on the motif itself, but also on three-dimensional structure and surrounding amino acid environment (Bader et al. 2008, BMC Microbiol. 8: 116.). BLAST analysis and sequence alignment of EpxL-RT with the sequences of Epx1 homologs of other yeasts (e.g. *Saccharomyces cerevisiae, Candida* ssp) revealed that the KR motif in the leader sequence is not conserved. Therefore, processing of the KR motif by proteases such as Kex2 could not be assumed a priori based on sequence analysis.

Example 5: Construction of a *P. pastoris* Host Cell Line for the Expression of Recombinant Proteins Using the *P. pastoris* EpxL-KR Sequence (Truncated Leader, SEQ ID 10, Wherein X at Position 3 is F, and X at Position 16 is A (SEQ ID 12)) for Secretion In order to test if the KR sequence in EpxL-RT truly is a protease cleavage site, vectors for the expression of recombinant proteins using the EpxL-KR sequence for secretion were constructed.

5a) Construction of a *P. pastoris* Strain Overexpressing HSA Using the EpxL-KR Sequence for Secretion.

HSA was amplified using the primers in Table 4.1, and ligated into the vector pPM2_pGAPxLRT digested with BgII and SbfiI. After sequence verification, the vector pPM2_pGAPxLKR-HSA was linearized in the promoter region and transformed into *P. pastoris*.

TABLE 4.1

Oligonucleotide primers for PCR amplification of HSA fused to EpxL-KR (restriction sites are underlined, the EpxL sequence is in italics)

| | | |
|---|---|---|
| EpxL-KR_HSA forw | BglI | SEQ ID 32<br>ATTC*GCCGAAGAGGCAGCAAACCACTTGCACAAGCG TGATGCACACAAGAGTGAGGTT* |
| HSA back | SfiI | SEQ ID 33<br>GAGTGGCCGAGGCGGCCTTATAAGCCTAAGGCAGCT TGA |

5b) Construction of a *P. pastoris* Strain Overexpressing Porcine Trypsinogen or eGFP Using the EpxL-KR Sequence for Secretion.

pTRP was amplified using the primers in Table 4.2, and ligated into the vector pPM2_pGAPxLRT digested with PvuII and SbfiI. The expression vector pPM2_pGAPxLKR-eGFP was generated in the same way. After sequence verification, the vectors pPM2_pGAPxLKR-pTRP and pPM2_pGAPxLKR-eGFP were linearized in the promoter region and transformed into *P. pastoris*.

TABLE 4.2

Oligonucleotide primers for PCR amplification of pTRP or eGFP fused to EpxL-KR (restriction sites are underlined, the EpxL sequence is in italics)

| | | |
|---|---|---|
| EpxL-KR-pTRP forw | PvuII | SEQ ID 34<br>ATAC<u>CAGCTGCTCCAGTTGCTCCAGCCGAAGAGG</u> *CAGCAAACCACTTGCACAAGCG*TACTGACGACGA CGACAAG |
| pTRP back | SfiI | SEQ ID 35<br>TTTT<u>GGCCGAGGCGGCC</u>TTTCAGTTAGCAGCGAT AGTTTG |

TABLE 4.2-continued

Oligonucleotide primers for PCR amplification of pTRP or eGFP fused to EpxL-KR (restriction sites are underlined, the EpxL sequence is in italics)

| | |
|---|---|
| EpxL-KR- PvuII eGFP forw | SEQ ID 36<br>ATAC<u>CAGCTG</u>*CTCCAGTTGCTCCAGCCGAAGAGG CAGCAAACCACTTGCACAAGCGTGTGAGCAAGG GCGAGGAGC* |
| eGFP back SfiI | SEQ ID 37<br>CGTT<u>GGCCGAGGCGGCC</u>TTACTTGTACAGCTCGT CCATG |

5c) Construction of a *P. pastoris* Strain Overexpressing Antibody Light Chain or Heavy Chain Using the EpxL-KR Sequence for Secretion.

The light chain (LC) and the heavy chain (HC) of the antibody HyHEL were amplified using the primers in Table 4.3, and ligated into the vector pPM2_pGAPxLRT digested with BgIII and SbfI. After sequence verification, the vectors pPM2_pGAPxLKR-LC and pPM2_pGAPxLKR-HC were linearized in the promoter region and transformed into *P. pastoris*.

TABLE 4.3

Oligonucleotide primers for PCR amplification of HyHEL LC or HC fused to EpxL-KR (restriction sites are underlined, the EpxL sequence is in italics)

| | |
|---|---|
| EpxL-KR- BglI LC forw | SEQ ID 38<br>ATA*A<u>GCCGAAGAGGC</u>AGCAAACCACTTGCACAAGCGT GACATCGTTTTG* |
| LC back SfiI | SEQ ID 39<br>CTAT<u>GGCCGAGGCGGCC</u>CTATTAACACTCACCTCTGT TG |
| EpxL-KR- BglI HC forw | SEQ ID 40<br>ATA*A<u>GCCGAAGAGGC</u>AGCAAACCACTTGCACAAGCGT GACGTTCAATTG* |
| HC back SfiI | SEQ ID 41<br>TATC<u>GGCCGAGGCGGCC</u>CTATTACTTACCTGGGGACA AG |

Example 6: Expression of Recombinant Proteins by a *P. pastoris* Host Cell Line Using the EpxL-KR (Truncated Leader, SEQ ID 10, Wherein X at Position 3 is F, and X at Position 16 is A (SEQ ID 12) for Secretion 6a) Analysis of *P. pastoris* Overexpressing Recombinant Porcine Trypsinogen Using EpxL-KR for Secretion

*P. pastoris* expressing pTRP using the EpxL-KR sequence for secretion (Example 5b) were cultivated as described in Example 2a and analysed as in Example 3a.

Surprisingly, we observed that processing was indeed enhanced by using the shortened Epx secretion leader EpxL-KR (FIG. 4.1, middle part). Contrary to the protein smear observed when using EpxL-RT for secretion (FIG. 4.1, left part), secretion of pTRP using EpxL-KR yielded a band of the correct size (FIG. 4.1, middle part). The correct N-terminus of pTRP secreted using EpxL-KR was verified by mass spectrometric analysis (LC-MS).

Therefore approx. 10 µg of each sample were separated with SDS-PAGE and the desired protein bands were cut out and digested in gel. The proteins were carbamidomethylated in gel. The proteins were either digested with sequencing grade trypsin (Roche) or with Glu-C(Sigma-Aldrich), LysC (Roche) and Chymotrypsin (Roche) or analysed without digestion. All proteolytic reactions were performed at 37° C., overnight. Afterwards the samples were directly injected to the LC-MS system (LC: Dionex Ultimate 3000 LC, MS: Bruker, amaZon ETD, equipped with the on-line nano source). The peptides were separated on a C-18 Column (Dr. Maisch GmbH, C-18 HPLC column ReproSil-Pur 200*0.1 mm, 3 µm packing, 200 A pore diameter, flow: 0.4 µL/min) and a linear gradient from 95% solvent A and 5% solvent B (Solvent A: 0.1% FA in water, 0.1% FA in ACCN) to 32% B in 40 min was applied, followed by a 15 min linear gradient from 32% B to 75% B that facilitates elution of large peptides and analyzed by MS with data-dependent acquisition. Data were processed using standard Bruker software (data analysis) and the freeware program X!-tandem combined with GPM.

Contrary to the correct N-terminus of pTRP secreted with EpxL-KR, the amino acids EAEA were determined to be left at the N-terminus of secreted pTRP when using MFα for secretion. Moreover, the amount of pTRP secreted using EpxL-KR was more than 20% higher compared to the commonly used MFα-secretion leader (Table 5).

TABLE 5

Relative secretion levels of pTRP normalized to MFα

| Leader | Relative mean pTRP secretion ± SEM |
|---|---|
| EpxL-KR | 1.21 ± 0.02 |
| MFα | 1.00 ± 0.09 |

6b) Analysis of *P. pastoris* Overexpressing Recombinant Human Serum Albumin Using EpxL-KR for Secretion

*P. pastoris* expressing HSA using the EpxL-KR sequence for secretion (Example 5a) were cultivated as described in Example 2a and analysed using Western Blot (Example 2d).

Contrary to the double band pattern observed when using EpxL-RT for secretion (FIG. 2.3, left part), secretion of HSA using EpxL-KR yielded a single band of the correct size (not shown). Thus, EpxL-KR was able to secrete correctly processed HSA.

6c) Analysis of *P. pastoris* Overexpressing eGFP Using EpxL-KR for Secretion

*P. pastoris* expressing eGFP using the EpxL-KR sequence for secretion (Example 5b) were cultivated as described in Example 2a and analysed as in Example 3b.

Only the EpxL-KR leader led to correct size eGFP (FIG. 4.2, left side), whereas leftovers of the MFα leader led to higher molecular weight eGFP (FIG. 4.2, right side). LC-MS analysis (described in Example 6a) verified the correct N-terminus of eGFP secreted by EpxL-KR, which qualifies the secreted product for the content of molecules with the correct N-terminus of at least 95%, preferably at least 98%, even more preferred at least 99% or about 100% (w/w). In contrast, the use of MFα caused the amino acids EAEA leaving as additional amino acid sequence at the N-terminus due to incorrect processing of the leader peptide by Ste13 aminopeptidase. According to the band sizes on the SDS-PAGE, the majority of eGFP secreted by MFα possesses the incorrect amino acid overhangs EAEA at the N-terminus, whereas no band of incorrect size can be observed for eGFP secreted by EpxL-KR. As for pTRP (Example 6a), secretion levels of eGFP using EpxL-KR were more than 20% higher compared to using MFα (Table 6).

TABLE 6

Relative secretion levels of eGFP normalized to MFα
(quantified from band intensities with ImageJ software)

| Leader | Relative mean eGFP secretion ± SEM |
|---|---|
| EpxL-KR | 1.23 ± 0.05 |
| MFα | 1.00 ± 0.08 |

6d) Analysis of *P. pastoris* Overexpressing Antibody Light Chain or Antibody Heavy Chain Using EpxL-KR for Secretion

*P. pastoris* expressing either HyHEL LC or HyHEL HC using the EpxL-KR sequence for secretion (Example 5c) were cultivated as described in Example 2a and analysed as in Example 2d.

Both antibody chains could be secreted using the EpxL-KR sequence (FIG. 4.3), confirming EpxL-KR as valuable secretion leader for antibody production in *P. pastoris*. The correct N-terminus of HyHEL LC secreted by EpxL-KR was verified by LC-MS analysis as described in Example 6a.

Example 7: Construction of a *P. pastoris* Host Cell Line for the Expression of Recombinant Proteins Using the EpxL-AA Sequence (SEQ ID 21) for Secretion WO2010/135678 and US20110021378 describe the amino acid sequence of MKLSTNLILAIAAASAVVSAA (SEQ ID 21), i.e. amino acid 1-21 of SEQ ID 8, which corresponds to the first 21 amino acids of the full-length Epx1 leader. However, no experimental data is provided in WO2010/135678 and US20110021378 showing that this sequence would actually be suitable for secretion of recombinant proteins. In order to test if this fragment, called EpxL-AA thereafter, is sufficient to enable the secretion of correctly processed recombinant proteins, we constructed vectors for the expression of recombinant proteins using the EpxL-AA sequence for secretion.

Antibody light chain LC, pTRP, and eGFP were amplified using the primers in Table 7, and ligated into the vector pPM2_pGAPxLRT digested with BgII and SfiI. After sequence verification, the vectors pPM2_pGAPxLAA-LC, pPM2_pGAPxLAA-pTRP and pPM2_pGAPxLAA-eGFP were linearized in the promoter region and transformed into *P. pastoris*, respectively.

TABLE 7

Oligonucleotide primers for PCR amplification of pTRP, eGFP and HyHEL LC fused to EpxL-AA (restriction sites are underlined, the EpxL sequence is in italics)

| EpxL-AA-<br>LC forw | SbfI | SEQ ID 42<br>ATCA<u>CCTGCAGG</u>ATGAAGTTCTCCACCAATTTGA<br>*TTCTAGCTATTGCAGCAGCTTCCGCCGTTGTCTC<br>AGCTGCT*GACATCGTTTTGACTCAATCCCC |
|---|---|---|
| LC back | SfiI | SEQ ID 43<br>CTAT<u>GGCCGAGGCGGCC</u>CTATTAACACTCACCTC<br>TGTTG |
| EpxL-AA-<br>pTRP forw | PvuII | SEQ ID 44<br>ATAC<u>CAGCTG</u>CTACTGACGACGACGACAAG |
| pTRP back | SfiI | SEQ ID 45<br>TTTT<u>GGCCGAGGCGGCC</u>TTTCAGTTAGCAGCGAT<br>AGTTTG |
| EpxL-AA-<br>eGFP forw | PvuII | SEQ ID 46<br>GTAC<u>CAGCTG</u>CTGTGAGCAAGGGCGAGGAGC |
| eGFP back | SfiI | SEQ ID 47<br>CGTT<u>GGCCGAGGCGGCC</u>TTACTTGTACAGCTCGT<br>CCATG |

Example 8: Expression of Recombinant Proteins by a PA *Pastoris* Host Cell Line Using EpxL-AA (SEQ ID 21) for Secretion 8a) Analysis of *P. Pastoris* Overexpressing eGFP Using EpxL-AA for Secretion

*P. pastoris* expressing eGFP using the EpxL-AA sequence for secretion (Example 7) were cultivated as described in Example 2a and analysed as in Example 3b.

On the SIDS-PAGE, the size of the bands with EpxL-AA are slightly larger than with EpxL-KR (FIG. 5.1), which indicates that at least one Ala residue is left at the N-terminus of eGFP, thereby representing a non-native N-terminus of the recombinant secretory protein.

8b) Analysis of *P. pastoris* Overexpressing Recombinant Porcine Trypsinogen Using EpxL-AA for Secretion

*P. pastoris* expressing pTRP using the EpxL-AA sequence for secretion (Example 7) were cultivated as described in Example 2a and analysed as in Example 3a.

pTRP was secreted using the EpxL-AA sequence, however, secretion levels were lower than with the EpxL-KR sequence (Table 8). On the SDS-PAGE, the size of the bands with EpxL-AA are slightly larger than with EpxL-KR (FIG. 5.1), which indicates that at least one Ala residue is left at the N-terminus of pTRP.

Indeed, N-terminal sequencing of pTRP secreted by EpxL-AA revealed that the N-terminus of the recombinant secretory protein contained an additional amino acid, Ala, which remained from the EpxL-AA sequence, thereby representing a non-native N-terminus of the recombinant secretory protein.

TABLE 8

Relative secretion levels of pTRP normalized to EpxL-KR

| Leader | Relative mean pTRP secretion ± SEM |
|---|---|
| EpxL-KR | 1.00 ± 0.12 |
| EPxL-AA | 0.79 ± 0.04 |

8c) Analysis of *P. pastoris* Overexpressing LC Using EpxL-AA for Secretion

*P. pastoris* expressing HyHEL LC using the EpxL-AA sequence for secretion (Example 7) were cultivated as described in Example 2a and analysed as in Example 2d. For LC, secretion levels with EpxL-AA were lower as compared to EpxL-KR or MFalfa (FIG. 5.2). As for pTRP, N-terminal sequencing of LC secreted by EpxL-AA showed that the N-terminus of the recombinant secretory protein contained an additional amino acid, Ala, which remained from the EpxL-AA sequence.

This is again an unwanted residue derived from the signal sequence, rendering EpxL-AA unsuitable for the production of secreted recombinant proteins.

Example 9: Construction of a *P. pastoris* Host Cell Line for the Expression of Recombinant Proteins Using the EpxL-A Sequence (Signal Peptide Sequence, SEQ ID 1, Wherein X at Position 3 is F, and X at Position 16 is A, SEQ ID 3) for Secretion Therefore we constructed *P. pastoris* strains secreting recombinant proteins by a signal sequence consisting just of the first 20 amino acids of the native Epx1 leader, termed EpxL-A. The Ala represents the last amino acid before (C-terminal of) the predicted signal peptidase cleavage site, whereas on the N-terminal side of the SP cleavage site the recombinant protein starts immediately. In order to verify that the nature of this N-terminal amino acid does not influence cleaving of SP, we tested the secretion of three different recombinant proteins: eGFP (starting with the hydrophobic amino acid Val), and antibody LC and HC (starting with the negatively charged amino acid Asp).

Antibody light chain LC, Fab-HC, and eGFP were amplified using the primers in Table 9, and ligated into the vector pPM2_pGAPxLRT digested with BgII and SfiI. After sequence verification, the vectors were linearized in the promoter region and transformed into *P. pastoris*.

For LC and Fab-HC the pGAP promoter was also exchanged for the inducible pG1 promoter (SEQ ID 9) using ApaI and SbfI, then the expression cassettes for both chains were combined onto one vector by using the compatible restriction enzymes MreI and AgeI. After sequence verification, the vector was linearized in the AOX-TT region and transformed into *P. pastoris*.

Example 10: Expression of Recombinant Proteins by a *P. pastoris* Host Cell Line Using EpxL-A (Signal Peptide Sequence, SEQ ID 1, Wherein X at Position 3 is F, and X at Position 16 is A, SEQ ID 3) for Secretion 10a) Analysis of *P. pastoris* Overexpressing eGFP Using EpxL-A for Secretion

*P. pastoris* expressing eGFP using the EpxL-A sequence for secretion (Example 9) were cultivated as described in Example 2a and analysed as in Example 3b.

As can be seen in FIG. 5.1, secretion levels of eGFP using EpxL-A were comparable to EpxL-KR, and higher than with EpxL-AA.

Contrary to the hydrophobin signal and leader sequences described in Kottmaier et al. (2011 Appl Microbiol Biotechnol. 91: 133-141) and the MFα prepro-leader, the EpxL-A sequence and the EpxL-KR sequence do not result in vacuolar targeting of eGFP (as proven by confocal laser scanning microscopy—data not shown). Both strains exhibit an intracellular eGFP distribution representative for proteins present in the secretory pathway (staining mainly of the endoplasmic reticulum); therefore the EpxL-A signal peptide and the EpxL-KR truncated leader seem to be well suited for the secretion of recombinant proteins as they display a "secretory phenotype".

10b) Analysis of *P. pastoris* Overexpressing LC Using EpxL-A for Secretion

*P. pastoris* expressing HyHEL LC using the EpxL-A sequence for secretion (Example 9) were cultivated as described in Example 2a and analysed as in Example 6d.

The use of EpxL-A for secretion of antibody light chain led to a correctly sized protein (FIG. 5.2), whereby secretion was as efficient as with EpxL-KR and more than 8-fold higher than with EpxL-AA (Table 10). Secretion levels were compared by quantifying band intensities on the gel shown in FIG. 5.2 using ImageJ software.

TABLE 9

Oligonucleotide primers for PCR amplification of eGFP and HyHEL LC and Fab-HC fused to EpxL-A (restriction sites are underlined, the EpxL sequence is in italics)

| Name | Enzyme | Sequence |
|---|---|---|
| EpxL-A-LC forw | SbfI | SEQ ID 48<br>TACTCCTGCAGGATGAAGTTCTCCACCAATTTGATTCTAG<br>CTATTGCAGCAGCTTCCGCCGTTGTCTCAGCTGACGTTCA<br>ATTGCAAGAATCTGG |
| LC back | SfiI | SEQ ID 49<br>CTATGGCCGAGGCGGCCCTATTAACACTCACCTCTGTTG |
| EpxL-A-eGFP forw | PvuII | SEQ ID 50<br>GTACCAGCTGTGAGCAAGGGCGAGGAGC |
| eGFP back | SfiI | SEQ ID 51<br>CGTTGGCCGAGGCGGCCTTACTTGTACAGCTCGTCCATG |
| EpxL-A-Fab HC forw | SbfI | SEQ ID 52<br>TACTCCTGCAGGATGAAGTTCTCCACCAATTTGATTCTAG<br>CTATTGCAGCAGCTTCCGCCGTTGTCTCAGCTGACGTTCA<br>ATTGCAAGAATCTGG |
| Fab HC back | SfiI | SEQ ID 53<br>TCATGGCCGAGGCGGCCCTATTACTTGTCACAGGACTTTG<br>GCTC |

TABLE 10

Relative secretion levels of HyHEL LC normalized to EpxL-AA.

| Leader | Relative mean LC secretion ± SEM |
|---|---|
| EpxL-KR | 8.82 ± 0.53 |
| EPxL-AA | 1.00 ± 0.55 |
| EPxL-A | 9.53 ± 0.87 |

The N-terminus of LC secreted by EpxL-A was verified by LC-MS to be the correct N-terminus DIVLTQSP (Asp-Ile-Val-Leu-Thr-Gln-Ser-Pro, SEQ ID 54).

Therefore, the signal peptide of Epx1, EpxL-A, is sufficient and suitable for secreting recombinant proteins with correct N-terminus, contrary to the longer sequence EpxL-AA.

In addition to expression under the control of the constitutive pGAP promoter, secretion of LC with EpxL-A was also tested under the control of the inducible pG1 promoter (SEQ ID 9). Strain construction was described in Example 9. Glucose-limiting conditions in screening cultures were generated by using glucose feed beads as described in Example 2a). Under such inducing conditions, secretion of light chain was observed.

10c) Analysis of P. pastoris Overexpressing Antibody Fab Fragment Using EpxL-A for Secretion P. pastoris expressing the Fab fragment of HyHEL antibody (consisting of the light chain ($v_L$ and $c_L$) and the heavy chain fragment ($v_H$ and $c_{H1}$) using the EpxL-A sequence for secretion of both chains (strain described in Example 9) were cultivated as described in Example 2a and analysed as in Examples 2d and 2e.

Surprisingly, using the EpxL-A sequence for secretion of both LC and HC of HyHEL Fab, the levels of intact secreted Fab were up to ten-fold higher than with the MFα prepro leader (determined by ELISA as described in Example 2e). Fab yields per biomass were 0.15-0.35 mg Fab/OD when using EpxL-A, compared to 0.03-0.13 mg Fab/OD when using MFα for secretion. Furthermore, the supernatants of P. pastoris secreting HyHEL Fab under control of pG1 with EpxL-A do not contain high levels of free LC or higher molecular weight aggregates of the recombinant protein (FIG. 5.3).

Example 11: Expression of Recombinant Proteins by a P. pastoris Host Cell Line Using EpxL-A (Signal Peptide Sequence, SEQ ID 1, Wherein X at Position 3 is F, and X at Position 16 is A (SEQ ID 3) for Secretion The secretion of eight proteins from P. pastoris by the use of EpxL-A (SEQ ID 3) was tested: Human Growth Hormone (HGH), Somatotropin, Interferon alpha2a (IFN-α 2a), the two different his-tagged scFvs (scFvs1 and scFvs2) and the 3 different Fabs Fab1, Fab2 and Fab3.

The genes were codon optimized for P. pastoris and synthesized by GeneArt (Germany). The obtained vectors were digested with SbfI and SfiI and the genes were ligated into the vector pPM2aZ30_pG1. In case of Fabs, the expression cassettes for both chains were combined onto one vector by using the compatible restriction enzymes MreI and AgeI. After sequence verification, the vectors were linearized in the AOX terminator region and transformed into P. pastoris.

P. pastoris strains expressing the recombinant proteins Human Growth Hormone, Somatotropin, Interferon alpha2a, the two his-tagged scFvs scFv1 and scFv2 and the three Fabs Fab1, Fab2 and Fab3 (Fabs consisting of the light chain ($v_L$ and $C_L$) and the heavy chain fragment ($v_H$ and $c_{H1}$)) using the EpxL-A sequence (SEQ ID 3) for secretion were cultivated in medium containing per liter: 10 g yeast extract, 10 g peptone, 100 mM potassium phosphate buffer pH 6.0, 13.4 g yeast nitrogen base with ammonium sulfate and 0.4 mg biotin. Small scale screenings were performed in 24 well plates with two feed beads (Kuhner, diameter 6 mm).

Supernatants were analysed as in Example 2d. POIs were detected in Western Blots by use of specific antibodies: For Somatotropin and Human Growth Hormone: GH1 Polyclonal Antibody; proteintech 17867-1AP (1:5,000) and Anti-Rabbit IgG (whole molecule)-Alkaline Phosphatase antibody, Sigma A3687 (1:12,000). For Interferon-alpha 2a: Interferon, alpha 2a antibody; antibodies-online ABIN573795 (1:1,500) and Anti-Rabbit IgG (whole molecule)-Alkaline Phosphatase antibody, Sigma A3687 (1:12,000). For His-tagged scFvs: Penta-His HRP Conjugate; QIAGEN 10149928 (1:1,500).

All tested proteins were successfully secreted into the culture medium when the EpxL-A sequence (SEQ ID 3) was used (FIG. 6).

The invention claimed is:

1. A nucleic acid construct encoding a fusion of a signal peptide and a heterologous protein of interest (POI), wherein the signal peptide consists of the amino acid sequence SEQ ID NO:2;
   wherein the heterologous POI comprises one or more immunoglobulin variable domains, and wherein the heterologous POI does not comprise one or more immunoglobulin single variable domains;
   wherein the signal peptide is fused directly to the N-terminal amino acid residue of the heterologous POI, the N-terminal amino acid sequence of the POI is heterologous to the signal peptide, the N-terminal amino acid of the heterologous POI is not alanine, and the amino acid sequence of the fusion of the signal peptide and the heterologous POI does not comprise the signal peptidase cleavage site identified as SEQ ID NO: 6; and
   wherein the fusion of the signal peptide and the heterologous POI is cleaved between the C-terminal amino acid of the signal peptide and the N-terminal amino acid of the heterologous POI when expressed in a *Pichia pastoris* host cell.

2. An expression vector comprising the nucleic acid construct of claim 1, and a promoter which is operably linked to the nucleic acid encoding the signal peptide.

3. A recombinant yeast host cell comprising the nucleic acid construct of claim 1.

4. A recombinant yeast host cell comprising the expression vector of claim 2.

5. The host cell of claim 4, wherein the yeast is *Pichia pastoris*.

6. A method of producing a protein of interest (POI) in a yeast host cell, comprising:
   providing the host cell according to claim 3,
   cultivating said host cell to express said POI, and
   purifying the POI to obtain a preparation of a purified POI.

7. A method of producing a protein of interest (POI) in a yeast host cell, comprising:
   a) cultivating the host cell according to claim 3 in a culture medium under conditions such that said host cell expresses and/or produces the POI; and
   b) isolating and/or purifying the POI from the culture medium.

8. A method for the expression of a heterologous protein of interest B (POI) comprising one or more immunoglobulin variable domains, said method comprising the steps of:
   a) introducing into a host cell a vector comprising a nucleic acid construct encoding a fusion of a signal peptide and the heterologous protein of interest (POI), wherein the signal peptide consists of the amino acid sequence SEQ ID NO:2;
   wherein the signal peptide is fused directly to the N-terminal amino acid residue of the heterologous POI, the N-terminal amino acid sequence of the POI is heterologous to the signal peptide, the N-terminal amino acid of the heterologous POI is not alanine, and the amino acid sequence of the fusion of the signal peptide and the heterologous POI does not comprise the signal peptidase cleavage site identified as SEQ ID NO: 6; and
   wherein the fusion of the signal peptide and the heterologous POI is cleaved between the C-terminal amino acid of the signal peptide and the N-terminal amino acid of the heterologous POI when expressed in a *Pichia pastoris* host cell; and
   wherein the heterologous POI comprises one or more immunoglobulin variable domains and wherein the heterologous POI does not comprise one or more immunoglobulin single variable domains;
   b) cultivating the host cell in a culture medium under conditions that are such that said host cell expresses the secreted polypeptide; and
   c) isolating and/or purifying the secreted polypeptide from the culture medium.

9. The method of claim 8, wherein the host cell is a *Pichia pastoris* cell.

* * * * *

UNITED STATES PATENT AND TRADEMARK OFFICE
CERTIFICATE OF CORRECTION

PATENT NO. : 11,359,223 B2
APPLICATION NO. : 15/860186
DATED : June 14, 2022
INVENTOR(S) : Brigitte Gasser et al.

Page 1 of 1

It is certified that error appears in the above-identified patent and that said Letters Patent is hereby corrected as shown below:

On the Title Page

Item (57) Lines 8-10 of the Abstract: "of the specific nucleic acid for the secretion of a POT from a host cell and/or to increase the secretion of a POT from a host cell" should be replaced with --of the specific nucleic acid for the secretion of a POI from a host cell and/or to increase the secretion of a POI from a host cell--.

In the Claims

Column 58, Line 8-9 (Claim 8): "heterologous protein of interest B (POI)" should be replaced with --heterologous protein of interest (POI)"--.

Signed and Sealed this
Twenty-seventh Day of September, 2022

Katherine Kelly Vidal
*Director of the United States Patent and Trademark Office*